(12) United States Patent
Visser et al.

(10) Patent No.: US 7,223,740 B2
(45) Date of Patent: May 29, 2007

(54) VECTORS FOR ENHANCED EXPRESSION OF VEGF FOR ATRIAL DISEASE TREATMENT

(75) Inventors: Tjerk Johannes A. Visser, Amsterdam (NL); Folkert Feiko Roossien, Muiden (NL); Carola Jacoba M. Ubink-Bontekoe, Nunspeet (NL)

(73) Assignee: Fornix Biosciences N.V., Lelystad (NL)

( * ) Notice: Subject to any disclaimer, the term of this patent is extended or adjusted under 35 U.S.C. 154(b) by 0 days.

(21) Appl. No.: 10/478,449

(22) PCT Filed: May 23, 2002

(86) PCT No.: PCT/NL02/00326

§ 371 (c)(1),
(2), (4) Date: Apr. 29, 2004

(87) PCT Pub. No.: WO02/095038

PCT Pub. Date: Nov. 28, 2002

(65) Prior Publication Data

US 2005/0090464 A1  Apr. 28, 2005

(30) Foreign Application Priority Data

May 23, 2001  (EP) .................. 01201944

(51) Int. Cl.
*A61K 48/00* (2006.01)
*C12N 15/00* (2006.01)

(52) U.S. Cl. ..................... 514/44; 435/320.1
(58) Field of Classification Search ............ 435/252.3, 435/320.1, 325; 514/44
See application file for complete search history.

(56) References Cited

U.S. PATENT DOCUMENTS 5,830,879 A  11/1998  Isner 5,919,652 A  7/1999  Pang et al.

FOREIGN PATENT DOCUMENTS

| EP | 0 561 034 | 9/1993 |
| WO | WO 9947690 | 9/1999 |
| WO | WO 0061751 | 10/2000 |

OTHER PUBLICATIONS

Baumgartner et al, Circulation, 97:1114-1123, 1998.*
Neufeld et al, FASEB Journal, 13:9-22, 1999.*
Daniel et al, Plant Molecular Biology, 28:821-836, 1995. Abstract only.*
Isner et al, Lancet, 348:370-374, 1996.*
Schaper et al, Cardiovascular Research, 43:835-837, 1999.*
Schwartz et al, Gene Therapy, 3:405-411, 1996.*
Dente et al, Nucleic Acids Research, 11:1645-1655, 1983.*
Yla-Herttuala, Lancet, 355:213-222, 2000.*
Gardlik et al, Medical Science Monitor, 11:RA110-RA121, 2005.*
Romano et al, Stem Cells, 18: 19-39, 2000.*
Romano Drug News Perspect, 17(2): 85-90, 2004.*
Database EMBL Online, retrieved from EBI, Database Accession No. AF264696, XP002180574.
Database EMBL Online, retrieved from EBI, Database Accession No. U47120, XP002180575.

* cited by examiner

*Primary Examiner*—Deborah Crouch
*Assistant Examiner*—Magdalene Sgagias
(74) *Attorney, Agent, or Firm*—Amster, Rothstein & Ebenstein LLP

(57) ABSTRACT

The invention provides a vector which is capable of the expression of a vascular endothelial growth factor wherein the vector comprises a modified PCMV promoter. The invention further provides use of a vector which is capable of and expressing a vascular endothelial growth factor (VEGF) for the regulation of endothelial function, angiogenesis and arteriogenesis. The invention further comprises use of a vector which is capable of the expression of a vascular endothelial growth factor (VEGF) for the prophylactic treatment of arterial diseases and/or bone marrow diseases and/or neural diseases.

7 Claims, 2 Drawing Sheets

Figure 1. Plasmid phVEGF165.MB sequence

Sequence:

```
   1 GAATTCGAGC TCGCCCCGTT ACATAACTTA CGGTAAATGG CCCGCCTGGC
  51 TGACCGCCCA ACGACCCCCG CCCATTGACG TCAATAATGA CGTATGTTCC
 101 CATAGTAACG CCAATAGGGA CTTTCCATTG ACGTCAATGG GTGGAGTATT
 151 TACGGTAAAC TGCCCACTTG GCAGTACATC AAGTGTATCA TATGCCAAGT
 201 ACGCCCCCTA TTGACGTCAA TGACGGTAAA TGGCCCGCCT GGCATTATGC
 251 CCAGTACATG ACCTTATGGG ACTTTCCTAC TTGGCAGTAC ATCTACGCGC
 301 GCTACGTATT AGTCATCGCT ATTACCATGG TGATGCGGTT TTGGCAGTAC
 351 ATCAATGGGC GTGGATAGCG GTTTGACTCA CGGGGATTTC CAAGTCTCCA
 401 CCCCATTGAC GTCAATGGGA GTTTGTTTTG GCACCAAAAT CAACGGGACT
 451 TTCCAAAATG TCGTAACAAC TCCGCCCCAT TGACGCAAAT GGGCGGTAGG
 501 CGTGTACGGT GGGAGGTCTA TATAAGCAGA GCTCGTTTAG TGAACCGTCA
 551 GATCGCCTGG AGACGCCATC CACGCTGTTT TGACCTCCAT AGAAGACACC
 601 GGGACCGATC CAGCCTCCGG GGATCTTGG TGGCGTGAAA CTCCCGCACC
 651 TCTTCGGCCA GCGCCTTGTA GAAGCGCGTA CGATGAACTT TCTGCTGTCT
 701 TGGGTGCATT GGAGCCTTGC CTTGCTGCTC TACCTCCACC ATGCCAAGTG
 751 GTCCCAGGCT GCACCCATGG CAGAAGGAGG AGGGCAGAAT CATCACGAAG
 801 TGGTGAAGTT CATGGATGTC TATCAGCGCA GCTACTGCCA TCCAATCGAG
 851 ACCCTGGTGG ACATCTTCCA GGAGTACCCT GATGAGATCG AGTACATCTT
 901 CAAGCCATCC TGTGTGCCCC TGATGCGATG CGGGGGCTGC TGCAATGACG
 951 AGGGCCTGGA GTGTGTGCCC ACTGAGGAGT CCAACATCAC CATGCAGATT
1001 ATGCGGATCA AACCTCACCA AGGCCAGCAC ATAGGAGAGA TGAGCTTCCT
1051 ACAGCACAAC AAATGTGAAT GCAGACCAAA GAAAGATAGA GCAAGACAAG
1101 AAAATCCCTG TGGGCCTTGC TCAGAGCGGA GAAAGCATTT GTTTGTACAA
1151 GATCCGCAGA CGTGTAAATG TTCCTGCAAA AACACAGACT CGCGTTGCAA
1201 GGCGAGGCAG CTTGAGTTAA ACGAACGTAC TTGCAGATGT GACAAGCCGA
1251 GGCGGTGAGG ATCCTGAGAA CTTCAGGGTG AGTTTGGGGA CCCTTGATTG
1301 TTCTTTCTTT TTCGCTATTG TAAAATTCAT GTTATATGGA GGGGGCAAAG
1351 TTTTCAGGGT GTTGTTTAGA ATGGGAAGAT GTCCCTTGTA TCACCATGGA
1401 CCCTCATGAT AATTTTGTTT CTTTCACTTT CTACTCTGTT GACAACCATT
1451 GTCTCCTCTT ATTTTCTTTT CATTTTCTGT AACTTTTTCG TTAAACTTTA
1501 GCTTGCATTT GTAACGAATT TTTAAATTCA CTTTTGTTTA TTTGTCAGAT
1551 TGTAAGTACT TTCTCTAATC ACTTTTTTTT CAAGGCAATC AGGGTATATT
1601 ATATTGTACT TCAGCACAGT TTTAGAGAAC AATTGTTATA ATTAAATGAT
1651 AAGGTAGAAT ATTTCTGCAT ATAAATTCTG GCTGGCGTGG AAATATTCTT
1701 ATTGGTAGAA ACAACTACAC CCTGGTCATC ATCCTGCCTT TCTCTTTATG
1751 GTTACAATGA TATACACTGT TTGAGATGAG GATAAAATAC TCTGAGTCCA
1801 AACCGGGCCC CTCTGCTAAC CATGTTCATG CCTTCTTCTC TTTTCCTACAG
1851 CTCCTGGGCA ACGTGCTGGT TGTTGTGCTG TCTCATCATT TTGGCAAAGA
1901 ATTCACTCCT CAGGTGCAGG CTGCCTATCA GAAGGTGGTG GCTGGTGTGG
1951 CCAATGCCCT GGCTCACAAA TACCACTGAG ATCTTTTTCC CTCTGCCAAA
2001 AATTATGGGG ACATCATGAA GCCCCTTGAG CATCTGACTT CTGGCTAATA
2051 AAGGAAATTT ATTTTCATTG CAATAGTGTG TTGGAATTTT TTGTGTCTCT
2101 CACTCGGAAG GACATATGGG AGGGCAAATC ATTTAAAACA TCAGAATGAG
2151 TATTTGGTTT AGAGTTTGGC AACATATGCC CATATGCTGG CTGCCATGAA
2201 CAAAGGTTGG CTATAAAGAG GTCATCAGTA TATGAAACAG CCCCCTGCTG
2251 TCCATTCCTT ATTCCATAGA AAAGCCTTGA CTTGAGGTTA GATTTTTTTT
2301 ATATTTTGTT TTGTGTTATT TTTTCTTTA ACATCCCTAA AATTTTCCTT
2351 ACATGTTTTA CTAGCCAGAT TTTTCCTCCT CTCCTGACTA CTCCCAGTCA
2401 TAGCTGTCCC TCTTCTCTTA TGGAGATCCC TCGAGGAGCT TTTTGCAAAA
2451 GCCTAGGTAA TGAATCGGCC AACGCGCGGG GAGAGGCGGT TTGCGTATTG
2501 GGCGCTCTTC CGCTTCCTCG CTCACTGACT CGCTGCGCTC GGTCGTTCGG
2551 CTGCGGCGAG CGGTATCAGC TCACTCAAAG GCGGTAATAC GGTTATCCAC
2601 AGAATCAGGG GATAACGCAG GAAAGAACAT GTGAGCAAAA GGCCAGCAAA
2651 AGGCCAGGAA CCGTAAAAAG GCCGCGTTGC TGGCGTTTTT CCATAGGCTC
2701 CGCCCCCCTG ACGAGCATCA CAAAAATCGA CGCTCAAGTC AGAGGTGGCG
2751 AAACCCGACA GGACTATAAA GATACCAGGC GTTTCCCCCT GGAAGCTCCC
2801 TCGTGCGCTC TCCTGTTCCG ACCCTGCCGC TTACCGGATA CCTGTCCGCC
2851 TTTCTCCCTT CGGGAAGCGT GGCGCTTTCT CATAGCTCAC GCTGTAGGTA
2901 TCTCAGTTCG GTGTAGGTCG TTCGCTCCAA GCTGGGCTGT GTGCACGAAC
2951 CCCCCGTTCA GCCCGACCGC TGCGCCTTAT CCGGTAACTA TCGTCTTGAG
3001 TCCAACCCGG TAAGACACGA CTTATCGCCA CTGGCAGCAG CCACTGGTAA
```

Figure 1, Contd.

```
3051 CAGGATTAGC AGAGCGAGGT ATGTAGGCGG TGCTACAGAG TTCTTGAAGT
3101 GGTGGCCTAA CTACGGCTAC ACTAGAAGAA CAGTATTTGG TATCTGCGCT
3151 CTGCTGAAGC CAGTTACCTT CGGAAAAAGA GTTGGTAGCT CTTGATCCGG
3201 CAAACAAACC ACCGCTGGTA GCGGTGGTTT TTTTGTTTGC AAGCAGCAGA
3251 TTACGCGCAG AAAAAAAGGA TCTCAAGAAG ATCCTTTGAT CTTTTCTACG
3301 GGGTCTGACG CTCAGTGGAA CGAAAACTCA CGTTAAGGGA TTTTGGTCAT
3351 GAGATTATCA AAAAGGATCT TCACCTAGAC TGCCAGTCAA AGCCACGTTG
3401 TGTCTCAAAA TCTCTGATGT TACATTGCAC AAGATAAAAA TATATCATCA
3451 TGAACAATAA AACTGTCTGC TTACATAAAC AGTAATACAA GGGGTGTTAT
3501 GAGCCATATT CAACGGGAAA CGTCTTGCTC GAGGCCGCGA TTAAATTCCA
3551 ACATGGATGC TGATTTATAT GGGTATAAAT GGGCTCGCGA TAATGTCGGG
3601 CAATCAGGTG CGACAATCTA TCGATTGTAT GGGAAGCCCG ATGCGCCAGA
3651 GTTGTTTCTG AAACATGGCA AAGGTAGCGT TGCCAATGAT GTTACAGATG
3701 AGATGGTCAG ACTAAACTGG CTGACGGAAT TTATGCCTCT TCCGACCATC
3751 AAGCATTTTA TCCGTACTCC TGATGATGCA TGGTTACTCA CCACTGCGAT
3801 CCCCGGGAAA ACAGCATTCC AGGTATTAGA AGAATATCCT GATTCAGGTG
3851 AAAATATTGT TGATGCGCTG GCAGTGTTCC TGCGCCGGTT GCATTCGATT
3901 CCTGTTTGTA ATTGTCCTTT TAACAGCGAT CGCGTATTTC GTCTCGCTCA
3951 GGCGCAATCA CGAATGAATA ACGGTTTGGT TGATGCGAGT GATTTTGATG
4001 ACGAGCGTAA TGGCTGGCCT GTTGAACAAG TCTGGAAAGA AATGCATAAG
4051 CTTTTGCCAT TCTCACCGGA TTCAGTCGTC ACTCATGGTG ATTTCTCACT
4101 TGATAACCTT ATTTTTGACG AGGGGAAATT AATAGGTTGT ATTGATGTTG
4151 GACGAGTCGG AATCGCAGAC CGATACCAGG ATCTTGCCAT CCTATGGAAC
4201 TGCCTCGGTG AGTTTTCTCC TTCATTACAG AAACGGCTTT TTCAAAAATA
4251 TGGTATTGAT AATCCTGATA TGAATAAATT GCAGTTTCAT TTGATGCTCG
4301 ATGAGTTTTT CTAATCAGAA TTGGTTAATT GGTTGTAACA CTGGCAGAGC
4351 ATTACGCTGA CTTGACGGGA CGGCGGCTTT GTTGAATAAA TCGAACTTTT
4401 GCTGAGTTGA AGGATCAGAT CACGCATCTT CCCGACAACG CAGACCGTTC
4451 CGTGGCAAAG CAAAAGTTCA AAATCACCAA CTGGTCCACC TACAACAAAG
4501 CTCTCATCAA CCGTGGCTCC CTCACTTTCT GGCTGGATGA TGGGGCGATT
4551 CAGGCCTGGT ATGAGTCAGC AACACCTTCT TCACGAGGCA GACCTCAGCG
4601 CCCCCCCCCC CCGTTCTTCG GGGCGAAAAC TCTCAAGGAT CTTACCGCTG
4651 TTGAGATCCA GTTCGATGTA ACCCACTCGT GCACCCAACT GATCTTCAGC
4701 ATCTTTTACT TTCACCAGCG TTTCTGGGTG AGCAAAAACA GGAAGGCAAA
4751 ATGCCGCAAA AAAGGGAATA AGGGCGACAC GGAAATGTTG AATACTCATA
4801 CTCTTCCTTT TTCAATATTA TTGAAGCATT TATCAGGGTT ATTGTCTCAT
4851 GAGCGGATAC ATATTTGAAT GTATTTAGAA AAATAAACAA ATAGGGGTTC
4901 CGCGCACATT TCCCCGAAAA GTGCCACCTG ACGTCTAAGA AACCATTATT
4951 ATCATGACAT TAACCTATAA AAATAGGCGT ATCACGAGGC CCTTTCGTCT
5001 CGCGCGTTTC GGTGATGACG GTGAAAACCT CTGACACATG CAGCTCCCGG
5051 AGACGGTCAC AGCTTGTCTG TAAGCGGATG CCGGGAGCAG ACAAGCCCGT
5101 CAGGGCGCGT CAGCGGGTGT TGGCGGGTGT CGGGGCTGGC TTAACTATGC
5151 GGCATCAGAG CAGATTGTAC TGAGAGTGCA CCATATGCGG TGTGAAATAC
5201 CGCACAGATG CGTAAGGAGA AAATACCGCA TCAGGAAATT GTAAGCGTTA
5251 ATATTTTGTT AAAATTCGCG TTAAATTTTT GTTAAATCAG CTCATTTTTT
5301 AACCAATAGG CCGAAATCGG CAAAATCCCT TATAAATCAA AGAATAGAC
5351 CGAGATAGGG TTGAGTGTTG TTCCAGTTTG GAACAAGAGT CCACTATTAA
5401 AGAACGTGGA CTCCAACGTC AAAGGGCGAA AAACCGTCTA TCAGGGCGAT
5451 GGCCCACTAC GTGAACCATC ACCCTAATCA AGTTTTTTGG GGTCGAGGTG
5501 CCGTAAAGCA CTAAATCGGA ACCCTAAAGG GAGCCCCCGA TTTAGAGCTT
5551 GACGGGGAAA GCCGGCGAAC GTGGCGAGAA AGGAAGGGAA GAAAGCGAAA
5601 GGAGCGGGCG CTAGGGCGCT GGCAAGTGTA GCGGTCACGC TGCGCGTAAC
5651 CACCACACCC GCCGCGCTTA ATGCGCCGCT ACAGGGCGCG TCCATTCGCC
5701 ATTCAGGCTG CGCAACTGTT GGGAAGGGCG ATCGGTGCGG GCCTCTTCGC
5751 TATTACGCCA GCTGGCGAAA GGGGGATGTG CTGCAAGGCG ATTAAGTTGG
5801 GTAACGCCAG GGTTTTCCCA GTCACGACGT TGTAAAACGA CGGCCAGTGA
5851 ATTGTAATAC GACTCACTAT AGGGC
```

VECTORS FOR ENHANCED EXPRESSION OF VEGF FOR ATRIAL DISEASE TREATMENT

This application is a national stage entry under 35 U.S.C. §371 of PCT International Application No. PCT/NL02/00326, filed May 23, 2002, which claims priority of U.S. patent application Ser. No. 09/873,109, filed Jun. 1, 2001 now abandoned, and of European Patent Application No. 01201944.4, filed May 23, 2001, the contents of which are incorporated herein by reference in their entirety.

The invention relates to the field of medicine. In particular it relates to the treatment of disease more specifically arterial diseases and/or bone marrow diseases and/or neural diseases and/or inflammatory disorders.

In mammalian vascular development mesoderm-derived cells differentiate into endothelial cells that coalesce into blood vessels in a process called vasculogenesis. The formation of new blood vessels from pre-existing endothelium is termed angiogenesis. Several markers are consistently associated with embryonic stem (ES) cell-derived precursor cells having vascular potential, including the vascular endothelial growth factor (VEGF) receptor flk-1, the cell adhesion receptor platelet endothelial cell adhesion molecule (PE-CAM), and the adhesion molecule VE-cadherin.

VEGF-A functions in the development of embryonic structures during tissue remodelling and for the growth of tumour-induced vasculature. In solid tumors there is a constant requirement for vascular supply. Tumor-associated neovascularization is important for tumor cells to express their critical growth advantage. Experimental and clinical evidence suggests that the process of metastasis, is angiogenesis-dependent. Angiogenesis is a crucial process for tumor growth, metastasis and inflammation. Various angiogenic growth factors and cytokines induce neovascularization in tumors, namely members of the vascular endothelial growth factor (VEGF) and angiopoietin (Ang) gene families. Vascular endothelial growth factor (VEGF) is thought to be the most potent angiogenic factor in numerous malignant tumors and is a prognostic indicator for cancer patients. A strong correlation has been found between VEGF expression and increased tumor microvasculature, malignancy, and metastasis, for example in breast cancer. Vascular endothelial growth factor (VEGF) signaling is required for both differentiation and proliferation of vascular endothelium. VEGF-A stimulates many actions of endothelial cells including proliferation, migration, and nitric oxide release via binding to and activation of the two primarily endothelial-specific receptor-tyrosine kinases KDR and Flt-1. KDR and Flt-1 stimulate multiple signal transduction pathways in endothelial cells. These molecules also have in vivo expression patterns that are consistent with their being early markers of vascular lineage. VEGF signaling is critical for blood vessel formation during development.

In mouse VEGF is a 45-kd homodimer produced at sites of vasculogenesis and angiogenesis, and alternative splicing results in 3 different isoforms. The homodimer of VEGF-165 is the most active form and its properties include mitogenesis, chemotaxis, and permeability for endothelial cells. VEGF binds to 2 high-affinity receptors, flk-1 (VEGFR-2) and flt-1 (VEGFR-1), that are expressed in endothelium. Recently, a third molecule that binds VEGF with high affinity was identified as neuropilin-1, a receptor that also signals in the nervous system through a different ligand. Available data suggest that neuropilin-1 acts as a coreceptor with flk-1 in vascular tissues. Expression patterns of receptors and ligands suggest that VEGF may be a highly specific mediator of blood vessel formation in vivo, and analysis of targeted mutations in the mouse supports this hypothesis. Both flk-1 and flt-1 receptor mutations are recessive embryonic lethals at days 8.5 to 9.5 of gestation. The flk-1 mutation severely impairs vasculogenesis and hematopoiesis, whereas the flk-1 mutation affects vascular organization. Recent findings suggest that VEGF signaling is required for the transition of flk-1+ and PECAM+ cells to vascular endothelial cells that express ICAM-2 and CD34.

Dominantly acting transforming oncogenes are generally considered to contribute to tumor development and progression by their direct effects on tumor cell proliferation and differentiation. The growth of solid tumors beyond 1–2 mm in diameter requires the induction and maintenance of a tumor blood vessel supply, which is attributed in large part to the production of angiogenesis promoting growth factors by tumor cells. The mechanisms which govern the expression of angiogenesis growth factors in tumor cells are largely unknown, but dominantly acting oncogenes are thought to have a much greater impact than hitherto realised. An example of this is the induction of expression of vascular endothelial growth factor/vascular permeability factor (VEGF/VPF) by mutant H- or K-ras oncogenes, as well as v-src and v-raf, in transformed fibroblasts or epithelial cells. Tumor-derived vascular endothelial growth factor (VEGF)/vascular permeability factor (VPF) plays an important role in neovascularization and the development of tumor stroma. Besides VEGF/VPF, mutant ras genes are known to up-regulate the expression of a variety of other growth factors thought to have direct or indirect stimulating effects on angiogenesis, e.g. TGF-beta and TGF-alpha. This effect may be mediated through the ras-raf-MAP kinase signal transduction pathway, resulting in activation of transcription factors such as AP1, which can then bind to relevant sites in the promoter regions of genes encoding angiogenesis growth factors. In principle, similar events could take place after activation or over-expression of many other oncogenes, especially those which can mediate their function through ras-dependent signal transduction pathways.

Excess blood vessel formation contribute to initiating and maintaining many diseases such as chronic inflammatory disorders, tumor growth, restenosis, and atherosclerosis. In contrast insufficient blood vessel formation is responsible for tissue ischemia, as in coronary artery disease. The treatment of vascular disease although greatly improved over recent decades by drug medication, surgical and minimally-invasive techniques, remains limited by vascular proliferative lesions and by our inability to modulate the progression of native disease. An increasing number of patients with advanced coronary artery disease remain symptomatic despite maximal interventional, surgical or medical treatment. Ideally, they would benefit most from additional arterial blood supply to ischemic areas of myocardium. The invention discloses a novel therapeutic strategy for the treatment of vascular disease using the angiogenic growth factor VEGF. Previous therapeutic strategies using VEGF comprising proteins and/or plasmids were not able to produce VEGF polypeptide in a mammalian cells in sufficient quantities to improve neovascularisation or regional myeardial blood flow.

BRIEF DESCRIPTION OF THE DRAWING

FIG. 1. Plasmid phVEGF165.MB sequence (SEQ ID NO:6)

The invention provides a vector which is capable of effecting the expression of a vascular endothelial growth factor (VEGF or a functional equivalent thereof) in the appropriate environment wherein said vector comprises a modified pCMV promoter. The definition "functional equivalent" (homologue) means that a particular subject sequence varies from the reference sequence by one or more substitutions, deletions, or additions resulting in a sequence that encodes the same activity as VEGF in kind, not necessarily in amount. A vector capable of the effecting the expression of VEGF as used herein is a vector comprising a VEGE nucleic acid, that is at least capable of being expressed in the appropriate environment (i.e. a vector that is at least operative in mammalian systems). Preferably said vector comprises a plasmid. Preferably said modified pCMV promoter comprises the insertion of a 9 bp nucleic acid sequence ACGCGCGCT (SEQ ID NO:1), wherein A is a deoxyadenyl, G is deoxyguanyl, C is deoxycytosyl and T is thymidyl. pCMV promoter refers to the human cytomegalovirus (CMV) promoter. It is understood that (single) base substitutions may be made in said promoter sequence that will not significandy affect the function of the sequence.

The invention also provides a vector capable of effecting expression of VEGF, which lacks CpG-rich regions. Prior art vectors often had ampicillin resistance sequences or other sequences promoting immunogenicity such as CpG-islands. This may have contributed to the lack of efficacy in the prior art.

The invention provides a vector capable of effecting the expression of a vascular endothelial growth factor (VEGF) wherein said vector comprises an antibiotic resistance gene. Preferably said antibiotic resistance gene comprises kanamycin. Even more preferred said vector comprises a 5' HSV translation initiation signal and/or a β-globin splicing/adenylation signal. Also considered are all viral and eukaryotic, preferably mammalian, translation initiation signals and splicing/adenylation signals. Exogenous transcriptional elements and initation codons can be used and also can be of various origins, both natural and synthetic. The invention further provides a vector which is capable of effecting the expression of a vascular endothelial growth factor (VEGF), wherein said vector comprises a ColE1-like replicon and/or an F1 replication origin. ColE1-like replicons (e.g., pBR322) and other ColE1-like replicons (pMB1-, p15A, RSF1030-, and CloDF13-derived) in *E. coli* are considered suitable. F1 replication origin refers to phage F1 origin. All known replication origins previously defined and yet to be defined are deemed suitable. The efficiency of expression may be enhanced by the inclusion of enhancers appropriate for and least operative in mammalian systems.

In a preferred embodiment the invention provides a vector capable of effecting the expression of a vascular endothelial growth factor (VEGF), wherein said vascular endothelial growth factor (VEGF) is derived from a mammal. Preferably said mammal is a human. The invention further provides a vector capable of effecting the expression of a vascular endothelial growth factor (VEGF), wherein said vector comprises a vascular endothelial growth factor (VEGF) nucleic acid. Nucleic acid as used herein refers to an oligonucleotide, nucleotide or polynucleotide, and fragments or portions thereof, and to DNA or RNA of genomic or synthetic origin which may be single- or double-stranded, and represents the sense or antisense strand. It is understood that it is advantageous to increase the production of the endogenous vascular endothelial growth factor (VEGF) in a mammalian system, to promote angiogenesis, for example for the prophylactic treatment of arterial diseases and/or bone marrow diseases and/or neural diseases and/or inflammatory disorders, in particular tissue ischemia especially associated with diabetes. In a preferred embodiment said nucleic acid is operative in mammalian systems.

In the case of mammalian expression vectors, the expression of a nucleic acid of the invention may be driven by a number of previously defined and yet to be defined promoters, including inducible, developmentally regulated and tissue specific promoters. Promoters or enhancers derived from the genomes of mammalian cells are considered suitable. The invention further provides the use of the individual promoter of the nucleic acid of the present invention for this purpose. In particular any promoters of nucleic acids particularly involved in the regulation of endothelial function, angiogenesis or arteriogenesis are deemed suitable.

The invention provides a vector according to the invention wherein said vector can replicate to a high copy number in a bacterial cell. The invention further provides a host cell which comprises a vector according to the invention. The definition host cell as used herein refers to a cell in which an foreign process is executed by bio-interaction, irrespective of the cell belonging to a unicellular, multi-cellular, a differentiated organism or to an artificial cell or cell culture. Preferably said host cell is a mammalian cell, more preferred a human cell. The invention provides a host cell which contains within its genome a recombinant nucleic acid according the invention.

In a preferred embodiment the invention provides use of a vector which is suitable and capable of effecting the expression of a vascular endothelial growth factor (VEGF) according to the invention for the regulation of endothelial function. Vascular endothelial growth factor (VEGF) is also a specific endothelial cell mitogen that stimulates endothelial function and angiogenesis and plays a crucial role in tumor growth/angiogendsis. VEGF has a variety of effects on vascular endothelium, including the ability to promote endothelial cell viability, mitogenesis, chemotaxis, and vascular permeability. Vascular endothelial growth factor-A (VEGF-A) acts on endothelial cells and monocytes, two cell types that participate in the angiogenic and arteriogenic process in vivo. Monocytes are important in arteriogenesis and that their ability to migrate may be critical to the arteriogenic response. VEGF-A stimulates monocyte migration in healthy individuals.

The invention further provides use of a vector which is suitable and capable of effecting the expression of a vascular endothelial growth factor (VEGF) according to the invention for the regulation of angiogenesis. VEGF signaling is critical for blood vessel formation during development. VEGF plays an important role in the development of the vascular system, wound healing, vascularization of tumors, and for angiogenesis in ischemic tissues including the heart. The invention provides for use of a vector according to the invention for promoting neovascularization of ischemic tissues, as a preventative treatment or early stage treatment of cardiovascular diseases. VEGF-A can initiate the process of vascularization by stimulating chemoattraction and proliferation of angioblasts and endothelial cells [i.e. VEGF-A expression can stimulate angiogenic remodeling]. VEGF is also a potent vasodilating agent. The invention provides for use of a vector according to the invention for promoting neovascularization of wounds. VEGF expression is involved not only the formation of a vascular network but also promotes tissue formation. VEGF is also required for the cyclical blood vessel proliferation in the female reproductive tract.

The invention further comprises the use of a vector which is suitable and capable of effecting the expression of a vascular endothelial growth factor (VEGF) according to the invention for the regulation of arteriogenesis. In a preferred embodiment the invention provides the use of a vector according to the invention for the regulation of coronary and peripheral artery angiogenesis. VEGF-A plays a role as an endogenous activator of coronary collateral formation in the human heart. In a preferred embodiment said vector capable of effecting the expression of VEGF according the invention can be used in the prophylactic treatment of myocardial tissue (diseases), and also in the reconstructing process of infarcted myocardial tissue.

The invention further provides use of a vector according to the invention to induce the release of hematopoietic growth factors by bone marrow endothelial cells. VEGF is also required for longitudinal bone growth and endochondral bone formation. VEGF can induce the release of hematopoietic growth factors (GM-CSF) by bone marrow endothelial cells. In a preferred embodiment said vector capable of effecting the expression of VEGF according to the invention can be used to induce the release of hematopoietic growth factors, for example GM-CSF, to accelerate hematologic recovery after bone marrow grafting. Hematopoietic growth factors can mobilize peripheral blood stem cells from the bone marrow to therapeutically intervene in accelerating hematologic recovery. In a preferred embodiment said vector capable of effecting the expression of VEGF according to the invention may be used for the prophylactic treatment of haematological and oncological diseases. Preferably said vector capable of effecting the expression of VEGF according to the invention may be used to release hematopoietic growth factors in tissues after myeloablative chemotherapy and hematopoietic stem cell grafting. This can reduce the mortality related to autologous and allogeneic graft failure (i.e. bone marrow grafting). The invention further provides a vector capable of effecting the expression of VEGF according to the invention may be used to release hematopoietic growth factors which may be used to increase the quality of cytapheresis peripheral stem cell harvesting.

The invention further provides use of a vector capable of effecting the expression of VEGF according to the invention to induce transendothelial progenitor cell migration. Preferably to induce stromal cell-derived factor-1 (SDF-1) driven transendothelial progenitor cell migration. In the presence of VEGF in-vitro stromal cell-derived factor-1 (SDF-1) can drive and thus increase transendothelial progenitor cell migration. This may be due to pore formation (increased endothelial fenestration). Transendothelial migration of progenitors in vitro is substantially enhanced by the chemokine stromal-cell-derived factor-1 (SDF-1), which is produced by bone marrow stromal cells. More primitive progenitors also respond to this chemokine. Transendothelial progenitor cell migration is regulated by adhesion molecules, paracrine cytokines, and chemokines. Mobilizing hematopoietic growth factors stimulate proliferation of hematopoietic cells, which may indirectly result in changes of the local cytokine and chemokine milieu, adhesion molecule expression, and eventually the mobilization of hematopoietic progenitor cells.

The invention provides use of a vector capable of effecting the expression of VEGF according to the invention to increase endothelial fenestration. In tissues outside the brain, vascular endothelial growth factor-A (VEGF) causes vascular hyper-permeability by opening of inter-endothelial junctions and induction of fenestrations and vesiculo-vacuolar organelles (VVOs).

The invention provides use of a vector capable of effecting the expression of VEGF according to the invention to modulate neuroblastoma cell growth. VEGF may affect neuroblastoma cell growth directly and could be an autocrine growth factor. In a preferred embodiment said vector capable of effecting the expression of VEGF according the invention can be used in the prophylactic treatment of neural diseases, and in the reconstruction process after neural injury.

Critical Limb Ischemia and Diabetes Mellitus

Critical limb ischemia is one of the most burdensome problems in diabetes treatment, and provides a major challenge for VEGF gene transfer:

Patients with diabetes mellitus have a 20-fold risk of developing clinical peripheral arterial disease, a 17-fold increased risk of developing foot gangrene, and a 15-fold increased risk of amputation. In the Netherlands in 1992, 1810 amputations were performed. Actually 50% of lower leg amputations in non-trauma patients is performed in diabetes mellitus. Patients with diabetes mellitus have after unilateral amputation a 40–55% risk of amputation of the contralateral limb in the next 5 years. While the mean admission duration for clinical cases with a primary diagnosis of peripheral arterial disease is 12.2 days, this increases to 30 days in diabetes mellitus. Thus, in diabetes mellitus the prevalence of CLI is not only increased, but its course is markedly more serious.

The localization of macrovascular lesions (stenosis/occlusions) in diabetes mellitus shows a predilection for distal vessels. Especially involvement of vessels below the knee is prominent. On top of this, microvascular involvement is specific for diabetes mellitus. The localization of these lesions makes them less accessible to conventional forms of revascularisation (surgery, PTA, stent).

The current range of treatment options in CLI in diabetic foot disease is quite small. If possible revascularisation procedures are performed, and in case of superimposed infections aggressive antibiotic treatment is given. However, medical treatment is limited to prostacyclin analogues and attempts to improve tissue oxygenation with rheological means (e.g. Isodex), both with limited success. Initial results from a clinical study show less amputations and better limb survival of as a result of the VEGF treatment for the mentioned disease. Thus gene transfer of a VEGF vector according to the invention is useful for the treatment of tissue ischemia.

The invention further provides use of a vector capable of effecting the expression of VEGF according to the invention in the preparation of a composition. Suitable base for compositions are known in the art. The invention further provides a composition comprising a vector capable of effecting the expression of VEGF according to the invention. Preferably said composition is in a form that can be administered to a mammal. A preferred embodiment is that said composition is suitable for human external application, for example wound healing.

The invention also provides a composition comprising a vector capable of effecting the expression of VEGF according to the invention which is a pharmaceutical. Suitable pharmaceutical compositions are known and they may be in dosage forms such as tablets, pills, powders, suspensions, capsules, suppositories, injection preparations, ointments, eye drops etc.

In a preferred embodiment the invention provides use of a composition according to the invention and/or a vector according to the invention for the treatment of arterial diseases and/or bone marrow diseases and/or neural diseases and/or inflammatory disorders, in particular tissue ischemia especially associated with diabetes. Modes of administration can readily be determined by conventional protocols. A preferable mode of administration is by syringe injection to a localized tissue.

The invention further comprises a method of treatment of arterial diseases and/or bone marrow diseases and/or neural diseases and/or inflammatory disorders and/or wounds comprising administering a vector according to the invention and/or a composition according to the invention with a carrier to a suitable recipient. Preferably said carrier is a pharmaceutically acceptable carrier (e.g. drug carrier system) or inert carrier.

EXAMPLES

Example 1

Construction of a Highly Efficient VEGF Expression Plasmid (phVEGF165.MB) Without an Ampicilline Resistant Gene Plasmid phVEGF165.MB (FIG. 1) was constructed from phVEGF165.SR, which was originally constructed by cloning a VEGF cDNA, obtained by RT-PCR of human vascular smooth muscle cells, into a eukaryotic expression vector (see Severne et al., 1988 and Isner et al., 1996 for details). The plasmid phVEGF165.SR (kindly provided by Isner), was re-sequenced. Besides a few mutations (including in the A-hdI site), an almost complete β-lactamase gene was found. The 3' part of the ampicillin resistance gene (751 bp) was deleted out of phVEGF165.SR.

Deleting of the 3' part of β-lactamase gene (751 bp)/Creating AhdI site:

The PCR-forward primer: 5'-ATCGACATCCAGT-CAAAGCCACGTTGTGTCTCA-3' (SEQ ID NO:2) (first 2 nucleotides are miscellaneous, followed by an AhdI site), and the PCR reverse primer: 5'-ATAGCATGC-GAGTTTCGCCCCGAAGA-3' (SEQ ID NO:3) were used to amplify kanamycin.

For ColE1-origin the forward primer: 5'-GCGGACTAGT-GCTGTCCCTCTTCTCTTATGA-3' (SEQ ID NO:4) and the backward or reversed primer: 5'GCCGACGTG-CAGTCTAGGTGAAGATCCTTTT-3' (SEQ ID NO:5) (increased with AhdI) were used.

Both PCR products were ligated to each other, using AhdI, in an pCR-BluntII-TOPO (Invitrogen). And after sequencing, the kanamycin/ori gene was digested with ClaI and BlnI, and ligated into the ClaI/BlnI sites of phVEGF165.SR. This resulted in a plasmid without ampicillin and with a new AhdI restriction site: phVEGF165.MB. The promotor region was changed during growth in the *E. Coli* DH5-alpha and included in this promoter was a 9 bp nucleic acid sequence ACGCGCGCT (SEQ ID NO:1) insertion. Synthesis of VEGF mRNA is driven by the modified cytomegalovirus (CMV) promoter. Downstream of the VEGF coding region is a rabbit β-globin sequence for splicing and polyadenylation. A 5' untranslated thymidine kinase sequence from herpes simplex virus (HSV) is used for translation initiation. The phVEGF165.MB plasmid harbours the kanamycin gene for selection during propagation in *E. Coli*.

| Positions in the plasmid: | | |
|---|---|---|
| 14–619 | CMV promoter/enhancer | CMV |
| 620–682 | 5'HSV translation initiation signal | 5'HSV |
| 682–1258 | VEGF coding sequence | VEGF |
| 1259–2180 | β-globin splicing/polyadenylation signal | pA |
| 2457–3370 | ColE1-like replicon | ori |
| 3388–4623 | kanamycin gene | kana |
| 4647–4724 | 5' part of β-lactamase gene | |
| 5238–5690 | f1 origin | f1 ori |
| 5854–5875 | T7 promoter | T7 |

Example 2

Detection of the Ability of the phVEGF165MB Plasmid to Transform COS7 Cells to Produce VEGF Protein 70% confluent COS7 cells were transfected with VEGF plasmid Fugene. After 3 and 4 days the VEGF concentration in the supernatant was detected with a VEGF R&D kit (ELISA). The VEGF production (n=3) on day 3 and 4 of the plasmids without (phVEGF165.SR) and with (phVEGF165.MB) the modified cytomegalovirus (CMV) promoter were respectively 1.3/1.5 and 1.4/1.6 (pg/ml per 10E6 COS cells).

Phase I clinical studies have established that intramuscular gene transfer may be utilized to successfully accomplish therapeutic angiogenesis.

Gene transfer was performed in ten limbs of nine patients with non-healing ischemic ulcers (n=7) and/or rest pain (n=10) due to peripheral arterial disease. A total amount of 4000 μg naked plasmid DNA encoding the secreted 165-amino acid isoform of human VEGF (phVEGF$_{165}$) was injected into ischemic muscles of the affected limb. The average follow-up was 6±3 (range 2 to 11) months. Local intramuscular gene transfer induced no or mild local discomfort up to 72 hours after the injection. Serial CPK measurements remained in the normal range and there were no signs of systemic or local inflammatory reactions. To date, no aggravated deterioration in eyesight due to diabetic retinopathy or growth of latent neoplasm has been observed in any patient treated with phVEGF$_{165}$ gene tranfer. The only complication observed in the trial, was limited to transient lower extremity edema, consistent with VEGF-enhancement of vascular permeability.

Transgene expression. Blood levels of VEGF transiently peaked one to three weeks post gene transfer in seven patients amenable for weekly assays. In two patients baseline and/or more than two follow-up blood samples were not achievable. Clinical evidence of VEGF (vascular permeability factor) overexpression was evident by the observation of peripheral edema development (+1 to +4 by gross inspection) in those six patients with ischemic ulcers. In four patients, the edema was limited to the treated limb, while in two patients the contralateral limb was affected as well, albeit less severely. Edema corresponded temporally to the rise in serum VEGF levels.

Noninvasive arterial testing. The absolute systolic ankle or toe pressure increased in nine limbs post gene transfer and was unchanged in one limb at the time of the most recent follow-up (p=0.008). The ABI and/or TBI increased from 0.33±0.04 (0.22 to 0.57, p=0.028, [n=10]) at four weeks; to 0.45±0.04 (0.27 to 0.59, p=0.016, [n=10]) at eight weeks; and to 0.48±0.03 (0.27 to 0.67, p=0.017, [n=8]) at 12 weeks.

Improvement in the pressure index was sustained, but did not further rise significantly after the second gene transfer.

Exercise performance improved in all five patients with rest pain or minor ischemic ulcers, who underwent a graded treadmill exercise. All patients experienced a significant increase in pain-free walking time (2.5±1.1 min pre gene therapy vs 3.8±1.5 min at an average of 13 weeks post gene therapy, p=0.043) and absolute, claudication-limited walking time (4.2±2.1 min vs 6.7±2.9 min, p=0.018). Two patients reached the target endpoint of ten minutes of exercise.

Angiography. Digital subtraction angiography showed newly visible collateral vessels at the knee, calf and ankle levels in six of ten ischemic limbs treated. The luminal diameter of the newly visible vessels ranged from 200 µm to >800 µm, although most were closer to 200 µm and these frequently appeared as a "blush" of innumerable collaterals. Collaterals did not regress in follow-up angiograms. Magnetic resonance angiography showed qualitative evidence of improved distal flow with enhancement of signal intensity as well as an increase in the number of newly visible collaterals in eight limbs.

Change in limb status and ischemic rest pain. Therapeutic benefit was demonstration by regression of rest pain and/or improved limb integrity. The frequency of ischemic rest pain expressed as afflicted nights per week decreased significantly (5.9±2.1 at baseline vs 1.5±2.8 at eight week follow-up, p=0.043), with a slight reduction of analgesic medication (on average from 1.8 to 1.5 analgetics/24 h period). Based on criteria proposed by Rutherford, limb status improved in nine of ten extremities treated. Moderate improvement, including both an upward shift in the clinical category (at least one clinical category in patients with rest pain and at least two categories to reach the level of claudication in patients with tissue loss) and an increase in the ABI>0.1 was documented in five cases. In one patient an ischemic ulcer resolved sufficiently to permit placement of a split-thickness skin grafting, leading to absolute limb salvage. In two patients, in whom a major amputation would have been inevitable, retention of a functional foot by a minor (toe) amputation was reached. Minimal improvement, including an upward shift in clinical category or improvement of the ABI>0.1 was present in another three cases. However, in two patients with and extensive forefoot necrosis and osteomyelitis a below-knee amputation was required despite significant hemodynamic and angiographic improvement. There was one patient with progressive toe gangrene, who remained unchanged from his hemodynamic and angiographic findings. The patient underwent a below-knee amputation eight weeks after gene therapy.

Immunohistochemistry and molecular analysis. Tissue specimens derived from one amputee ten weeks after gene therapy showed foci of proliferating endothelial cells. This finding was particularly striking with the fact in mind, that endothelial cell proliferation is nearly absent in normal arteries, is consistent with an estimated endothelias cell turnover time of "thousands of days" is quiescent microvasculature. PCR performed on these samples indicated persistence and widespread distribution of DNA fragments unique to phvEGF$_{165}$. Noteworthy amplification of DNA fragments was shown in muscle and skin samples derived from the site of injection as well as in several muscle samples remote from the site of injection. Southern blot analysis confirmed persistence of intact plasmid DNA in muscle specimen derived from two amputees eight and ten weeks after gene therapy.

Example 3

A Further Study was Performed to Determine the Effect of Treating Diabetic Patients with critical Limb Ischemia with VEGF Ischemic muscle represents a promising target for gene therapy with naked plasmid DNA. Intramuscular (IM) transfection of genes encoding angiogenic cytokines, particularly those which are naturally secreted by intact cells, may constitute an alternative treatment strategy for patients with extensive tissue ischemia, in whom contemporary therapies (pharmacologic interventions, angioplasty, bypass surgery) have previously failed or are not feasible. This strategy is designed to promote the development of supplemental collateral blood vessels that will constitute endogenous bypass conduits around occluded native arteries, a strategy termed "therapeutic angiogenesis".

Pre-clinical animal studies have indeed indicatedd that IM gene transfer may be utilized to successfully accomplish therapeutic angiogenesis. More recently, phase I clinical studies have indicated that IM gene transfer may be utilized to safely and successfully accomplish therapeutic angiogenesis in patients with critical limb ischemia.

At this moment there is no standard pharmacotherapeutic treatment. Antithrombotic and vasoactive drugs are of little value in the management of CLI. Only prostanoids have shown some efficacy, but there is no evidence that in the long-term the limb is saved.

The protocol outlined has been designed as a double blind placebo controlled phase III study of direct intramuscular gene transfer of phVEGF$_{165}$ in patients with critical limb ischemia (CLI).

The objectives are to determine the clinical response and physiologic extent of collateral artery development in patients receiving intramuscular phVEGF$_{165}$ gene transfer and the safety of this treatment on diabetic retinopathy and nephropathy compared with placebo. The primary endpoints are limb survival 100 days after the first IM injection with VEGF and an increase of ABI of 15%. A total of 60 adult men and women will participate in this study. Subjects will be eligible if they have critical limb ischemia, diabetes and not to be optimal candidates for surgical or percutaneous revascularization. The clinical response of subjects treated in this fashion will be evaluated by serial studies performed before and after treatment, non invasive perfusion techniques, capillary microscopy and PET.

Protocol

I. Therapeutic Angiogenesis is a Novel Strategy for the Treatment of Isehemia.

The therapeutic implications of angiogenic growth factors were identified by the pioneering work of Folkman and colleagues over two decades ago (1). Their work documented the extent to which tumor development was dependent upon neovascularization and suggested that this relationship might involve angiogenic growth factors which were specific for neoplasms. Beginning a little over a decade ago (2), a series of polypeptide growth factors were purified, and demonstrated to be responsible for natural as well as pathologic angiogenesis.

Subsequent investigations have established the feasibility of using recombinant formulations of such angiogenic growth factors to expedite and/or augment collateral artery development in animal models of myocardial and hindlimb ischemia. This novel strategy for the treatment of vascular insufficiency has been termed "therapeutic angiogenesis"

(3). The angiogenic growth factors first employed for this purpose comprised members of the FGF family. Baffour et al administered bFGF in daily intramuscular doses of 1 or 3 μg to rabbits with acute hindlimb ischemia; at the completion of 14 days of treatment, angiography and necropsy measurement of capillary density showed evidence of augmented collateral vessels in the lower limb, compared to controls (4). Pu et al used an acidic fibroblast growth factor (aFGP) to treat rabbits in which the acute effects of surgically-induced hindlimb ischemia were allowed to subside for 10 days before beginning a 10-day course of daily 4 mg IM injections; at the completion of 30 days follow-up, both angiographic and hemodynamic evidence of collateral development was superior to ischemic controls treated with IM saline (5). Yanagisawa-Miwa et al likewise demonstrated the feasibility of bFGF for salvage of infarcted myocardium, but in this case growth factor was administered intra-arterially at the time of coronary occlusion, followed 6 hrs later by a second intra-arterial bolus (6).

Isner used the same animal model developed by Pu et al (5) to investigate the therapeutic potential of a 45 kDa dimeric glycoprotein, vascular endothelial growth factor (VEGF), isolated initially as a heparin-binding factor secreted from bovine pituitary folliculo-stellate cells (7). VEGF was also purified independently as a tumor-secreted factor that induced vascular permeability by the Miles assay (8, 9), and thus its alternate designation, vascular permeability factor (VPF). Two features distinguish VEGF from other heparin-binding, angiogenic growth factors. First, the $NH_2$ terminus of VEGF is preceded by a typical signal sequence; therefore, unlike bFGF, VEGF can be secreted by intact cells (10). Second, its high-affinity binding sites, shown to include the tyrosine kinase receptors Flt-1 (11) and Flk-1/KDR (12, 13) are present on endothelial cells, but not other cell types; consequently, the mitogenic effects of VEGF—in contrast to acidic and basic FGF, both of which are known to be mitogenic for smooth muscle cells (14, 15) and fibroblasts as well as endothelial cells—are limited to endothelial cells (7, 16). (Interaction of VEGF with lower affinity binding sites has been shown to induce mononuclear phagocyte chemotaxis) (17, 18). Evidence that VEGF stimulates angiogenesis in vivo had been developed in experiments performed on rat and rabbit cornea (19, 20), the chorioallantoic membrane (7), and the rabbit bone graft model (20). The hypothesis was that the angiogenic potential of VEGF was sufficient to constitute a therapeutic effect (21). This hypothesis was confirmed after the administration of soluble 165-amino acid isoform of VEGF ($VEGF_{165}$) as a single intra-arterial bolus to the internal iliac artery of rabbits in which the ipsilateral femoral artery was excised to induce severe, unilateral hindlimb ischemia. Doses of 500–1.000 μg of VEGF produced statistically significant augmentation of angiographically visible collateral vessels, and histologically identifiable capillaries; consequent amelioration of the hemodynamic deficit in the ischemic limb was significantly greater in animals receiving VEGF than in non-treated controls (calf blood pressure ratio=0.75±0.14 vs 0.48±0.19, p<0.05). Serial (baseline, as well as 10 and 30 days post-VEGF) angiograms disclosed progressive linear extension of the collateral artery of origin (stem artery) to the distal point of parent-vessel (reentry artery) reconstitution in 7 of 9 VEGF-treated animals. Similar results were achieved in a separate series of experiments in which VEGF was administered by an intramuscular route daily for 10 days (22). These findings thus established proof of principle for the concept that the angiogene activity of VEGF is sufficiently potent to achieve therapeutic benefit.

While each of these studies documented an increase in the number of angiographically visible collaterals, and increased capillary density in the muscles studied at necropsy, evidence regarding the physiological consequences of such anatomical improvement was limited to blood pressure measurements recorded in the ischemic versus the normal limb. Accordingly, a series of studies in the ischemic hindlimb model in which an intra-arterial Doppler wire (23), sufficiently diminutive (0.018 in.) to measure phasic blood flow velocity in the rabbit's internal iliac artery, was used to investigate resting and maximum flow following therapeutic angiogenesis with a single, intra-arterial bolus of $VEGF_{165}$. By 30 days post-$VEGF_{165}$, flow at rest, as well as maximum flow velocity and maximum blood flow provoked by 2 mg papaverine were all significantly higher in the VEGF-treated group (24).

One of the distinguishing features of VEGF mentioned above—the fact that the VEGF gene encodes a secretory signal sequence—might be exploited as part of a strategy designed to accomplish therapeutic angiogenesis by arterial gene transfer. Previously was observed that site-specific transfection of rabbit ear arteries with the plasmid pXGH5 encoding the gene for human growth hormone—a secreted protein—yields local levels of human growth hormone equivalent to what has been considered to be in a physiologic range, despite the fact that immunohistochemical examination of the transfected tissue disclosed evidence of successful transfection in <1% of cells in the transfected arterial segment (25). Thus, gene products which are secreted may have profound biological effects, even when the number of transduced cells remains low. In contrast, for genes such as bFGF which do not encode a secretory signal sequence, transfection of a much larger cell population might be required for that intracellular gene product to express its biological effects.

Therefore, 400 μg of $phVEGF_{165}$ was applied, encoding the 165-amino acid isoform of VEGF, to the hydrogel layer coating the outside of an angioplasty balloon (26) and delivered the balloon catheter percutaneously to the iliac artery of rabbits in which the femoral artery had been excised to cause hindlimb ischemia. Site-specific transfection of $phVEGF_{165}$ was confirmed by analysis of the transfected internal iliac arteries using reverse transcriptase-polymerase chain reaction (RT-PCR) and then sequencing the RT-PCR product. Augmented development of collateral vessels was documented by serial angiograms in vivo, and increased capillary density at necropsy. Consequent amelioration of the hemodynamic deficit in the ischemic limb was documented by improvement in the calf blood pressure ratio (ischemic/normal limb) to 0.70±0.08 in the VEGF-transfected group vs 0.50±0.18 in controls (p<0.05). Algiographic and histologic evidence of angiogenesis were subsequently demonstrated following intra-arterial gene transfer of $phVEGF_{165}$ in a human patient (27). These findings established that site-specific gene transfer can be used to achieve physiologically meaningful therapeutic modulation of vascular disorders, including therapeutic angiogenesis. Of note, no study have disclosed any evidence of immunologic toxicity.

II. Critical Limb Ischemia and Diabetes Mellitus

Critical limb ischemia is one of the most burdensome problems in diabetes treatment, and provides a major challenge for VEGF gene transfer:

Patients with diabetes mellitus have a 20-fold risk of developing clinical peripheral arterial disease, a 17-fold increased risk of developing foot gangrene, and a 15-fold increased risk of amputation. In the Netherlands in 1992 1810 amputations were performed. Actually 50% of lower leg amputations in non-trauma patients is performed in diabetes mellitus. Patients with diabetes mellitus have after unilateral amputation a 40–55% risk of amputation of the contialateral limb in the next 5 years. While the mean admission duration for clinical cases with a primary diagnosis of peripheral arterial disease is 12.2 days, this increases to 30 days in diabetes mellitus. Thus, in diabetes mellitus the prevalence of CLI is not only increased, but its course is markedly more serious.

The localization of macrovascular lesions (stenosis/occlusions) in diabetes mellitus shows a predilection for distal vessels. Especially involvement of vessels below the knee is prominent. On top of this, microvascular involvement is specific for diabetes mellitus. The localization of these lesions makes them less accessible to conventional forms of revascularisation (surgery, PTA, stent).

The current range of treatment options in CLI in diabetic foot disease is quite small. If possible revascularisation procedures are performed, and in case of superimposed infections aggressive antibiotic treatment is given. However, medical treatment is limited to prostacyclin analogues and attempts to improve tissue oxygenation with rheological means (e.g. Isodex), both with limited success.

On the other hand, other diabetic complications may increase the risk of side effects of VEGF therapy in diabetes patients. Especially proliferative retinopathy, but also less outspoken forms of retinopathy and microalbuminuria might exacerbate in case of systemic effects of VEGF. Even the nature of the local abnormalities in CLI in diabetes might compromise beneficial effects of VEGF: in diabetes mellitus total skin flow is not necessarily reduced, but the contribution of nututive capillary versus shunt skin flow may be lowered. It is at this stage not known what effect intramuscular administration of VEGF may have on this distribution of skin flow, and, clinically, on ulcer healing.

In conclusion, CLI in patients with diabetes there is no standard treatment, VEGF may be increase both the chance of beneficial and unwanted effects of VEGF in patients with diabetes mellitus (41,42,43).

III. Gene Transfer of cDNA Encoding for Secreted Protein.

In experiments which have relied exclusively on the use of non-secreted gene products, examination by histochemical staining, in situ hybridization, and/or polymerase chain reaction has suggested that the transfection efficiency of direct gene transfer to vascular smooth muscle cells within the arterial wall was considerably less than 1% and might therefore preclude a meaningful biological response. In contrast, genes encoding for a secreted protein may overcome the handicap of inefficient transfection by a paracrine effect, secreting adequate protein to achieve local levels that may be physiologically meaningful. Nabel et al (28) demonstrated that despite similarly low efficiencies, cell surface protein expression resulting from percutaneous transfection of vascular smooth muscle cells with the histocompatibility gene HLA-B7 may be adequate to induce a biological response, namely, focal vasculitis. Necropsy evidence of a pathobiological response following arterial gene transfer was reported by the same group in the case of transgenes encoding for the secreted proteins PDGF-B (29) and FGF-1 (30); in the former study, only 0.1 to 1% of cells in the artery segment were estimated to contain plasmid DNA by PCR approximation. To more specifically determine the relation between a secreted gene product and transfection efficiency after in vivo arterial gene transfer, in vitro (31) and in vivo (25) models to serially monitor expression of a gene encoding for a secreted protein. In vivo analyses were performed using the central artery of the rabbit ear. Liposome-mediated transfection of plasmid DNA containing the gene for human growth hormone (hGH) was successfully performed in 18 of 23 arteries. Serum hGH levels measured 5 days after transfection ranged from 0.1 to 3.8 ng/mL (mean, 0.97 ng/mL); in contrast, serum drawn from the control arteries demonstrated no evidence of hGH production. Serial measurement of hGH from transfected arteries demonstrated maximum hGH secretion 5 days after transfection and no detectable hormone after 20 days. Despite these levels of secreted gene product documented in vivo, immunohistochemical staining of sections taken from the rabbit ear artery at necropsy disclosed evidence of successful transfection in <0.1% of cells in the transfected segment. Thus, low-efficiency transfection with a gene encoding for a secreted protein may achieve therapeutic effects not realized by transfection with genes encoding for proteins which remain intracellular.

In conclusion—in combination with the fact that ischemic skeletal muscle itself serves to augment transfection efficiency (32, 33)—similarly accounts for the bioactivity that is described above of gene transfer of naked DNA by direct injection into skeletal muscle (vide infra).

IV. Pre-clinical Animal Studies.

Ten days after ischemia was induced in one hindlimb of New Zealand White rabbits, 500 μg of phVEGF$_{165}$, or the reporter gene LacZ, were injected IM into the ischemic hindlimb muscles. Site-specific transgene expression was documented by mRNA and immunohistochemistry. At 30-day follow-up, angiographically recognizable collateral vessels and histologically identifiable capillaries were increased in VEGF-transfectants compared to controls. This augmented vascularity improved perfusion to the ischemic limb, as documented by a superior calf blood pressure ratio for phVEGF$_{165}$ (0.84±0.09) vs controls (0.67±0.06, p<0.1); by improved blood flow in the ischemic limb (measured using an intra-arterial Doppler wire) at rest (phVEGF$_{165}$=52.5±12.6, control=38.4±4.3, p<0.05); and by increased distribution of labeled microspheres to the adductor muscle (phVEGF$_{165}$=4.3±0.5, control=2.9±0.6 ml/min/100 g tissue, p<0.05), as well as the gastrocnemius muscle (phVEGF$_{165}$=3.9±0.8, control=2.8±0.9 ml/min/100 g tissue, p<0.05) of the ischemic limb. A more detailed description of this study has been published previously (32).

Ischemic muscle thus represents a promising target for gene therapy with naked plasmid DNA. IM transfection of genes encoding angiogenic cytokines, particularly those which are naturally secreted by intact cells, may constitute an alternative treatment strategy for patients with extensive tissue ischemia, in whom contemporary revascularization (anti-anginal medications, angioplasty, bypass surgery) have previously failed or are not feasible.

V. Phase I Clinical Studies.

Gene transfer was performed in ten limbs of nine patients with non-healing ischemic ulcers (n=7) and/or rest pain (n=10) due to peripheral arterial disease. A total amount of 4000 μg naked plasmid DNA encoding the secreted 165-animo acid isoform of human VEGF (phVEGF$_{165}$) was injected into ischemic muscles of the affected limb. The average follow-up was 6±3 (range 2 to 11) months. Local intramuscular gene transfer induced no or mild local discomfort up to 72 hours after the injection. Serial CPK measurements remained in the normal range and there were no signs of systemic or local inflammatory reactions. To date, no aggravated deterioration in eyesight due to diabetic retinopathy or growth of latent neoplasm has been observed in any patient treated with phVEGF$_{165}$ gene transfer. The only complication observed in the trial, was limited to transient lower extremity edema, consistent with VEGF-enhancement of vascular permeability (Baumgartner et al, Circ 1998; 97: 114–1123).

Transgene expression. Blood levels of VEGF transiently peaked one to three weeks post gene transfer in seven patients amenable for weekly assays. In two patients baseline and/or more than two follow-up blood samples were not achievable. Clinical evidence of VEGF (vascular permeability factor) overexpression was evident by the observation of peripheral edema development (+1 to +4 by gross inspection) in those six patients with ischemic ulcers. In four patients, the edema was limited to the treated limb, while in two patients the contralateral limb was affected as well, albeit less severely. Edema corresponded temporally to the rise in serum VEGF levels.

Noninvasive arterial testing. The absolute systolic ankle or toe pressure increased in nine limbs post gene transfer and was unchanged in one limb at the time of the most recent follow-up (p=0.008). The ABI and/or TBI increased from 0.33±0.04 (0.22 to 0.57, p=0.028, [n=10]) at four weeks; to 0.45±0.04 (0.27 to 0.59, p=0.016, [n=10]) at eight weeks; and to 0.48±0.03 (0.27 to 0.67, p=0.017, [n=8]) at 12 weeks. Improvement in the pressure index was sustained, but did not further rise significantly after the second gene transfer.

Exercise performance improved in all five patients with rest pain or minor ischemic ulcers, who underwent a graded treadmill exercise. All patients experienced a significant increase in pain-free walking time (2.5±1.1 min pre gene therapy vs 3.8±1.5 min at an average of 13 weeks post gene therapy, p=0.043) and absolute, claudication-limited walking time (4.2±2.1 min vs 6.7±2.9 min, p=0.018). Two patients reached the target endpoint of ten minutes of exercise.

Angiography. Digital subtraction angiography showed newly visible collateral vessels at the knee, calf and ankle levels in six of ten ischemic limbs treated. The luminal diameter of the newly visible vessels ranged from 200 µm to >800 µm, although most were closer to 200 µm and these frequently appeared as a "blush" of innumerable collaterals. Collaterals did not regress in follow-up angiograms. Magnetic resonance angiography showed qualitative evidence of improved distal flow with enhancement of signal intensity as well as an increase in the number of newly visible collaterals in eight limbs.

Change in limb status and ischemic rest pain. Therapeutic benefit was demonstration by regression of rest pain and/or improved limb integrity. The frequency of ischemic rest pain expressed as afflicted nights per week decreased significantly (5.9±2.1 at baseline vs 1.5±2.8 at eight week follow-up, p=0.043), with a slight reduction of analgesic medication (on average from 1.8 to 1.5 analgetics/24 h period). Based on criteria proposed by Rutherford, limb status improved in nine of ten extremities treated. Moderate improvement, including both an upward shift in the clinical category (at least one clinical category in patients with rest pain and at least two categories to reach the level of claudication in patients with tissue loss) and an increase in the ABI>0.1 was documented in five cases. In one patient an ischemic ulcer resolved sufficiently to permit placement of a split-thickness skin grafting, leading to absolute limb salvage. In two patients, in whom a major amputation would have been inevitable, retention of a functional foot by a minor (toe) amputation was reached. Minimal improvement, including an upward shift in clinical category or improvement of the ABI>0.1 was present in another three cases. However, in two patients with an extensive forefoot necrosis and osteomyelitis a below-knee amputation was required despite significant hemodynamic and angiographic improvement. There was one patient with progressive toe gangrene, who remained unchanged from his hemodynamic and angiographic findings. The patient underwent a below-knee amputation eight weeks after gene therapy.

Immunohistochemistry and molecular analysis. Tissue specimens derived from one amputee ten weeks after gene therapy showed foci of proliferating endothelial cells. This finding was particularly striking with the fact in mind, that endothelial cell proliferation is nearly absent in normal arteries, is consistent with an estimated endothelias cell turnover time of "thousands of days" is quiescent microvasculature. PCR performed on these samples indicated persistence and widespread distribution of DNA fragments unique to phVEGF$_{165}$. Noteworthy amplification of DNA fragments was shown in muscle and skin samples derived from the site of injection as well as in several muscle samples remote from the site of injection. Southern blot analysis confirmed persistence of intact plasmid DNA in muscle specimen derived from two amputees eight and ten weeks after gene therapy.

Experimental Design

A. Objectives

The scope of this double blind phase III study is to compare the treatment of intramuscular (IM) gene transfer of phVEGF$_{165s}$ in patients with critical limb ischemia with the standard treatment observation.

1. Primary Objectives

To determine the effect of intramuscular administration of 4000 µg phVEGF$_{165}$ on clinical, physiological parameters of critical limb ischemia and safety compared to the standard treatment.

2. Secondary Objectives

To determine and compare the effect on the quality of life for both treatments.

B. Selection of Patients

1. Inclusion Criteria

A total of 60 adult diabetic men and women will participate in this study. The restriction for diabetic patients provides a homogeneic population with similar vascular problems (peripheral vessels, frequently no alternative treatment, enough patients to participate). Subjects will be eligible if they have critical limb ischemia and have been judged not to be optimal candidates for surgical or percutaneous revascularization. Subjects must meet the following criteria to be eligible for study enrollment:

Male or female>18 years of age.

Both type I and type II diabetes mellitus patients are candidates.

Presence of critical limb ischemia, according to the following definitions (European Consensus Group on Critical Limb Ischemia):

rest pain and/or ischemic skin lesions, lasting for more than 2 weeks.

ankle systolic blood pressure <50 mmHg, or, in case of incompressible ankle vessels, toe systolic blood pressure <30 mmHg (44).

Not optimal candidates for surgical or percutaneous revascularization as determined by angiography.

2. Exclusion Criteria

Subjects who meet any of the following criteria will be excluded from the study enrollment:

Acute surgery necessary.

Pregnancy, lactation, or use of inadequate contraception.

Evidence of cancer (except low grade and fully resolved non-melanoma skin malignancy)

Preproliferative or proliferative diabetic retinopathy, or conditions obscuring ophthalmological inspection of the retina (e.c. cataract), based on fluorescein angiography of the retina. Patients without retinopathy or with background retinopathy are allowed.

Serum creatinine>200 μM.

Concurrent participation in a study using an experimental drug or an experimental procedure within the 28 days before VEGF gene transfer.

Other severe concurrent illness (e.g., active infection, severe congestive heart failure, or left ventricular ejection fraction [EF]<20%).

Bleeding diathesis, HIV infection, or any other condition that, in the opinion of the investigator, could pose a significant hazard to the subject if the investigational therapy was to be initiated.

Inability to follow the protocol and comply with follow-up requirements.

C. Dose and Administration

1. Dosage

The clinical study is performed as a double blind phase III study in 60 patients. In half of the patients a total dose of 4000 ug ph $VEGF_{165}$ will be given, each patient will receive 4 injections (each with 500 μg $phVEGF_{165}$), each with a volume of 1 ml. This will be repeated after 4 weeks (day 28). The other half of the patients will receive injections with physiologic salt without phVEGF.

2. Administration

The VEGF gene via a small needle (27 G) will be injected directly into the muscle. With echography the position of the needle will be checked. The spreading of the injectate into the muscle will also be monitored in this way. After introduction of the needle 5 ml of saline or saline containing 500 μg $phVEFG_{165}$ will be injected. This will be done at four different injection sites in gastrocnemius and anticus muscles.

D. Concomitant Therapy

No concomitant routine therapy will be excluded in this study. Subjects will be treated by their personal physicians with routine medication as needed. No restriction of medication will be stipulated. However, physicians will be encouraged not to change the established regimen of analgetics post intramuscular injections unless clearly indicated by a change in clinical status.

E. Pretreatment Assessments

Subjects will be screened prior to study initiation to determine their eligibility for the study based on the inclusion and exclusion criteria. Written informed consent will be obtained from subjects prior to intra muscular injections. To be eligible, the following assessments must be performed/obtained within 2 weeks prior to intramuscular injection unless otherwise indicated:

Medical history, including medications, demographic information, vascular history, and history of cancer.

Review of systems and specific emphasis on symptoms or history suggestive of tumors and on reproductive status.

Pain assessment by the McGill Pain Questionnaire and the pain rating index (PRI).

Vital signs (blood pressure, pulse, respirations, temperature).

Physical Examination:

Vascular status, using angiography and noninvasive vascular laboratory examinations, including ankle and toe pressures and Doppler spectral analysis or duplex examination of large lower extremity vessels. Criteria for CLI see above.

Detailed ophthalmological examination, including funduscopy, fundus photographs, and fluorescein angiography of retinal vessels.

Neurological examination, including quantified muscle force testing, neurographic examination of motor and sensory nerves of arm and leg, and quantified sensory examination.

Clinical Laboratory Samples:

SMAC-20 (sodium, potassium, bicarbonate, chloride, glucose, BUN, creatinine, albumin, alkaline phosphatase, bilirubin, calcium, creatine kinase, LDH, phosphate, SGOT [ALT] SGPT [AST], tropinins, CRP, total protein, uric acid, cholesterol, triglycerides; VEGF protein and plasmid; anti-dsDNA, two nightly portions of urine for micro-albuminuria).

Additional laboratory assessments: endothelial>markers=including: factor VIII-vWF, ICAM, VCAM, e-selectin.

CBC with manual differential and platelets.

Complete urinalysis, including dipstick for protein.

PT/aPTT or INR.

12-lead ECG.

Chest X-ray (posterior-anterior and lateral).

Serum pregnancy test for women of childbearing potential (within 24 hours prior to study drug administration).

F. Follow-Up Assessments

In hospital till three days after the injections: daily, vital signs, physical examination, use of analgetics, electrocardiogram, clinical laboratory testing (SMAC 20).

Follow-up clinic or office visit will be conducted when possible on an outpatient basis on Days 3, 7, 14 and 72 days after the intra muscular injections. The following assessments will be performed/obtained on Days 3, 7, 14 and 72 days unless otherwise indicated:

Vital signs (blood pressure, pulse, respirations, temperature).

Physical examination, including funduscopy.

Interval history (including medication changes) and review of systems.

Record the analgetics use in a diary.

Clinical laboratory samples SMAC-20 CBC with manual differential and platelets, urinalysis.

F1. Schedule of Evaluation

| | Pretreatment Day 0 | Day 0 VEGF im | Day 3 | Day 7 | Day 14 | Day 28 VEGF im | Day 31 | Day 35 | Day 42 | Day 100 | 1×/4 mo until 2 yr after 1st injection |
|---|---|---|---|---|---|---|---|---|---|---|---|
| History (analuse) | X | | X | X | X | X | X | X | X | X | X |
| QLC and pain | X | | | | | X | | X | X | X | |
| Vital signs | X | | X | X | X | X | X | X | X | X | |
| Physical examination | X | | X | X | X | X | X | X | X | X | X |
| 'SMAC-20' | X | | X | X | X | X | X | X | X | X | |
| Vascular techniques | X | | | | X | X | X | X | X | X | |
| Angiography | X | | | | | | | | | X | |
| ophthalmological examination | X | | | | | X | | | | X | |
| Neurologic examination | X | | | | | | | | | X | |
| PET scan | X | | | | | | | | | X | |

G. Analysis of Clinical Response

Patients will receive a diary to note their severity of pain (pain assessment by the McGill Pain Questionnaire and the PRI) and the daily use of analgetics. In the diary they also note their daily medication and activity.

H. Analysis of the Quality of Life

In this study the RAND-36 will be used to analyze the quality of life.

I. Analysis of Physiological and Anatomical Activity

On the specific vascular methods, and the choice of primary and secondary measures of effect:

The clinical course of an episode of CLI may be quite variable. Although in some patients an inexorable downhill course to amputation follows, in others slow healing of ulcers may occur. Several risk factors for an adverse outcome have been identified, such as diabetes, continued smoking, concurrent other cardiovascular disease or vascular laboratory parameters like low ankle or toe pressure or $TcPO_2$. However, unpredictability of ulcer healing in an individual patient stresses the importance of a controlled design in an intervention study. This is also the major flaw in the clinical studies of VEGF gene transfer in CLI reported so far.

The increase in ankle pressures and ABI reported in the studies of Isner et al of VEGF gene therapy in in CLI is remarkable. In fact non-revascularization interventions in CLI (medication, training) have never been reported to result in consistent increases in ankle pressures. In revascularisation studies a 15% increase in ankle pressures is considered to be clinically relevant (45, 46).

I1. Available Vascular Techniques.

For the primary measure of effect:

I1.1. Ankle- and Thigh-brachial and Toe-brachial Pressure and Index.

Using standard techniques and following AHA recommendations, the Doppler ankle blood pressure is measured and divided by a simultaneously measured brachial artery blood pressure (47). In short, using a 8 MHz Doppler probe forming part of a Parkes Doppler equipment audio Doppler signals are obtained over the posterior tibial and dorsalis pedis arteries of both feet. After suprasystolic inflation of previously applied cuffs adapted for ankle (12 cm wide) and thigh (18 cm wide) circumference, the ankle (and optionally: thigh) Doppler systolic blood pressure are measured during slow deflation. Measurements are made at rest. If the foot condition allows so, the measurement at rest will be followed by a measurement immediately after 3 minutes of exercise on a calf ergometer with a moment of 33 Nm. The toe pressure is determined using a toe cuff with photoplethysmographic assessment of the systolic blood pressure level during cuff deflation. Using an automated blood pressure meter simultaneous brachial artery blood pressures are obtained. The ankle-, thigh- and toe-brachial index is calculated by dividing the ankle blood pressure by the simultaneously measured brachial artery blood pressure. For the ankle blood pressure the highest of either posterior tibial or dorsalis pedis artery at rest is used, for the measurement after exercise the same foot artery is used. The CV of the measurements at rest has been found in several studies to be around 5% for intra-individual day-to-day comparisons (48, 49,50). For inter-individual comparisons of technicians the CV amounts to 8% (48). For a post-exercise ankle-brachial index the CV amounts to 9% (51).

For secondary measures of effect:

I.1.2. Flow in Calf/Forearm Using Strain Gauge Plethysmography.

Calf blood flow. Resting and maximal calf blood flow can be measured non-invasively by plethysmography, using an ECG-triggered venous occlusion plethysmograph with a pneumatically powered cuff inflator allowing rapid flow measurements. Flow measurements at rest are made in subjects by alternate occlusion and deflation of the cuffs during intervals of 5–6 heart beats, maximal blood flow is determined during the hyperemic response immediately following exercise. Measurements of the flow during exercise cannot be performed simply with venous occlusion plethysmography because the muscles move strongly and the volume changes during the contractions. Measurements of post-exercise hyperaemia, on the other hand, can be performed technically simply. Calf or forearm blood flow can be calculated from the rate of the initial increase in calf or arm circumference during venous occlusion and is expressed as milliliters per 100 ml of calf tissue per minute (52, 53, 54). Equipment is available for bilateral measurements at the Vascular laboratory of the Department of Medicine.

I.1.3. Skin Flow Assessment Using Laser Doppler Flowmetry.

Laser Doppler flowmetry is a technique for measuring changes in tissue blood flow. The method is based on the Doppler shift of monochromatic laser light scattered back by tissue. The Doppler signal is determined by the velocity and the number of moving scattering particles, mainly red blood cells and therefore is directly related to tissue blood flow rate. This non-invasive method is applicable to almost every tissue, although it has until now mainly been used for measuring skin blood flow. In the present study we will use a Diodop LDF meter, connected to a PC with self-developed software for signal analysis. Measurements will be made at rest after 3 minute of suprasystolic occlusion. A biological zero will be obtained. Local skin temperature will also be recorded using an Ellab thermocouple thermometer. Measurements will be performed at the medial malleolus of the treated leg, in case open lesions are present another site at the foot will be used (55, 56, 57, 58).

Optional (if possible combined with fluorescein angiography of the eyes):

I.1.4. Fluoresceine Capillary Microscopy.

In the skin the transcapillary diffusion of intravenously injected fluorescein is used to measure vascular permeability. Using single capillary fluorescein videodensitometry, Bollinger et al. have demonstrated that fluorescein diffusion in the skin is increased in a group of subjects with long-term diabetes mellitus (Boilinger 1982). This observation was confirmed by the same group, using a "large window" method (which is comparable to the method we used in our study), in which a larger number of capillaries, up to approximately 100, is studied. The large window method is, therefore, less sensitive for spatial and temporal changes in capillary flow. We have considerably improved the reproducibility of this method and thereby its value as a tool in intervention studies, without sacrificing its power to discriminate diabetic from normal subjects. Use is made of custom-made equipment, described elsewhere in detail (59, 60, 61, 62).

I.1.5. Positron Emission Tomography (PET).

Local perfusion and reduction of ischemic areas are to be detected by PET; $H_2O^{15}$-PET perfusion) or F-deoxyglucose (metabolism).

I.2. Ophthalmic Examination.

The following ophthalmic examinations will be conducted and recorded: Ophthalmic history, best corrected visual activity, slit-lamp biomicroscopy, intraocular pressure, fundus examination, fundusphotography and fluorescein angiography. Patients are categorized according to their clinical examination in having no retinopathy, background, preproliferative and proliferative diabetic retinopathy, based on the ETDRS international classification. Seven standard fundus photographs of both eyes are made through dilated pupils.

Fluorescein angiography in performed of the macular area of the right eye and of the mid periphery of both eyes in the late phases (64, 65, 66).

I.3. Neurologic Examination.

Neurological examination, the same measurements as performed at pretreatment assessment.

J. Follow-up Assessments:
  Physical examinations.
  Vascular techniques: angiography, ankle-, (optional) thigh-, and toe pressures and -brachial index, laser Doppler flowmetry. Before and at the end of follow-up.
  Ophthalmological examination; funduscopy and fundus photographs.
  Neurological examination.
  SMAC-20.

K. Potential Side Effects.

A. Complications related to diagnostic angiography such as rupture of an artery, infection, embolization, or allergic reactions to the contrast media used.

B. Even though we have attempted to minimize that risks associated with gene transfer by eliminating the need for any viral, liposomal or other vectors, it is recognized that theoretical risks of gene transfer remain. Though the DNA to be transferred is considered to be harmless, events could occur within normal cells that take up the foreign DNA that allow them to be transformed. Laboratory studies suggest that this is unlikely. We nevertheless acknowledge that cells could theoretically become abnormal after long periods of time.

C. Complications related to the VEGF protein. Until now only oedema of the treated limb has been described as minor complication. No evidence for systemic complications such as induction/exacerbation.

L. Definition of Response

Response will be defined as limb survival and/or improvement in ABI of 15%, as two independent variables. Limb survival is defined as absence of major amputation. Major amputations are those at the level of the ankle of higher.

M. Risk-Benefit Analysis

In the patient the major benefit we anticipate is to prevent major amputation. The risk can be toxicity as nephropathy, retinopathy and oedema and secondary infections due to the local injections.

On the basis of pre-clinical animal studies, we do not anticipate adverse consequences.

In the absence of gene transfer, deleterious consequences might include persistent rest pain, deterioration of the limb ischemia.

N. Evaluation of Safety

Following intramuscular injection toxicity will be evaluated to WHO criteria. No further injections will be given in case of any grade 3 or 4 toxicity with is caused by the intramuscular injections.

O. Statistics

The natural history for the need for major amputations of non reconstructable CLI (with ankle systolic pressure <50 mm Hg) is approximately 50% in 100 days. Based on the results of Isner demonstrating an approximately 50% salvage rate in limbs destined to be amputated when VEGF started, we hope for a substantial improvement in amputation rate. As treatments starts early we estimate that at least 50% of limbs at risk will not be deteriorate to the point of major amputation. From these patients who deteriorate a 50% salvage rate might still be feasible. Therefore, an improvement of approximately 50% major amputation to 12.5% is expected in this study. To detect the expected 37.5% improvement of limb survival (50% amputations to 12.5%) or a 50% improvement of ABI of 15% with the treatment of VEGF compared to the control group, 26 patients are needed in both groups (significance level of 0.05 (one-sided) and power 0.85; according to a binomial distribution). In total 60 patients will be entered because of a drop out percentage of appr. 10% in these group of patients. There will be a block randomization for two times 30 patients. After treating 30 patients there will be an interim analysis. The study will be stopped if there is a significant difference between both groups after 30 patients have been entered.

P. Subject Discontinuation

Subjects may discontinue the study at any time. If, in the judgment of the investigators, continuation in the study would be detrimental to the subject, the investigator may withdraw the subject at any time.

If a subject withdraws from the study after 24 hours, but before the safety and biologic activity follow-up period, he or she should be contacted in order to obtain information about the reason(s) for his or her withdrawal and the occurrence of any adverse events. The subject should be urged to return to the clinic for an early discontinuation visit to be assessed for safety and biologic response.

Q. Randomisation

This is a double blind placebo controlled phase III study. The placebo is produced in the pharmacy. There will be a block randomization for two times 30 patients and an interim analysis. Randomization will be done by sealed envelope method without replacement.

R. Results:

Preliminary results show that administration of VEGF gene to patients with critical limb ischemia has a distinct positive effect as compared tot the control group.

RERERENCES

1. Folkman J: Tumor angiogenesis: therapeutic implications. *N Engl J Med* 1971; 285: 1182–1186
2. Shing Y, Folkman J, Sullivan J, Butterfield R, Murray J, Klagsbrun M: Heparin-affinity purification of a tumor-derived capillary endothelial cell growth factor. *Science* 1984; 223: 1296–1299
3. White F C, Carroll S M, Magnet A, Bloor C M: Coronary collateral development in swine after coronary artery occlusion. *Circ Res* 1992; 71: 1490–1500
4. Baffour R, Berman J, Garb J L, Rhee S W, Kaufman J, Friedmann P: Enhanced angiogenesis and growth of collateral by in vivo administration of recombinant basic fibroblast growth factor in a rabbit model of acute lower limb ischemia: dose-response effect of basic fibroblast growth factor. *J Vasc Surg* 1992; 16: 181–191
5. Pu L Q, Sniderman A D, Brassard R, Lachapelle K J, Graham A M, Lisbona R, Symes J F: Enhanced revascularization of the ischemic limb by means of angiogenic therapy. *Circulation* 1993; 88: 208–215
6. Yanagisawa-Miwa A, Uchida Y, Nakamura F, Tomaru T, Kido H, Kamijo T, Sugimoto T, Kaji K, Utsuyama M, Kurashima C, Ito H: Salvage of infarcted myocardium by angiogenic action of basic fibroblast growth factor. *Science* 1992; 257: 1401–1403
7. Ferrara N, Henzel W J: Pituitary follicular cells secrete a novel heparin-binding growth factor specific for vascular endothelial cells. *Biochem Biophys Res Commun* 1989; 161: 851–855
8. Keck P J, Hauser S D, Krivi G, Sanzo K, Warren T, Feder J, Connolly D T: Vascular permeability factor, an endothelial cell mitogen related to PDGF. *Science* 1989; 246: 1309–1312
9. Connolly D R, Olander J V, Heuvelman D, Nelson R, Monsell R, Siegel N, Haymore B L, Leimgruber R S, Feder J: Human vascular permeability factor: isolation from U937 cells. *J Biol Chem* 1989; 264: 20017–20024
10. Leung D W, Cachianes G, Kuang W J, Goeddel D V, Ferrara N: Vascular endothelial growth factor is a secreted angiogenic mitogen. *Science* 1989; 246: 1306–1309
11. deVries C, Escobedo J A, Ueno H, Houck K, Ferrara N, Williams L T: Theins-like tyrosine kinase, a receptor for vascular endothelial growth factor. *Science* 1992; 255: 989–991
12. Millauer B, Wizigmann-Voos S, Schnurch H, Martinez R, Moller N P H, Risau W, Ulrich A: High affinity VEGF binding and developmental expression suggest Flk-1 as a major regulator of vasculogenesis and angiogenesis. *Cell* 1993; 72: 835–846
13. Terman B I, Dougher-Vermazen M, Carrion M E, Dimitrov D, Armellino D C, Gospodarowicz D, Bohlen P: Identification of the KDR tyrosine kinase as a receptor for vascular endothelial cell growth factor. *Biochem Biophys Res Commun* 1992; 187: 1579–1586
14. Klagsbrun M, D'Amore P A: Regulators of angiogenesis. *Annu Rev Physiol* 1991; 53: 217–239
15. Gospodarowicz D, Massoglia S, Cheng J, Fujii D K: Effect of fibroblast growth factor and lypoproteins on the proliferation of endothelial cells derived from bovine adrenal cortex, brain cortex, and corpus luteum capillaries. *J Cell Physiol* 1986; 127: 121–136
16. Conn G, Soderman D, Schaeffer M-T, Wile M, Hatcher V B, Thomas K A: Purification of glycoprotein vascular endothelial cell mitogen from a rat glioma cell fine. *Proc Natl Acad Sci USA* 1990; 87: 1323–1327
17. Shen H, Clauss M, Ryan J, Schmidt A-M, Tijburg P, Borden L, Connolly D, Stern D, Kao J: Characterization of vascular permeability factor/vascular endothelial growth factor receptors on mononuclear phagocytes. *Blood* 1993; 81: 2767–2773
18. Clauss M, Gerlach M, Gerlach H, Brett J, Wang F, Familletti P C, Dan Y-CE, Olander J V, Connolly D T, Stern D: Vascular permeability factor: a tumor-derived polypeptide that induces endothelial cell and monocyte procoagulant activity, and promotes monocyte migration. *J Exp Med* 1990; 172: 1535–1545
19. Levy A P, Tamargo R, Brem H, Nathans D: An endothelial cell growth factor from the mouse neuroblastoma cell fine NB41. *Growth Factors* 1989; 2: 9–19
20. Connolly D T, Hewelman D M, Nelson R, Olander J V, Eppley B L, Delfino J J, Siegel R N Leimgruber R S, Feder J: Tumor vascular permeability factor stimulates endothelial cell growth and angionenesis. *J Clin Invest* 1989; 84: 1470–1478
21. Takeshita S, Zheng L P, Brogi E, Kearney M, Pu L Q, Bunting S, Ferrara N, Symes J F, Isner J M: Therapeutic angiogenesis: A single intra-arterial bolus of vascular endothelial growth factor augments revascularization in a rabbit ischemic hindlimb model. *J Clin Invest* 1994; 93: 662–670
22. Takeshita S, Pu L-Q, Zheng L, Ferrara N, Stein L A, Sniderman A D, Isner J M, Symes J F: Vascular endothelial growth factor induces dose-dependent revascularization in a rabbit model of persistent limb ischemia. *Circulation* 1994; 90: II-228–II-234
23. Isner J M, Kaufman J, Rosenfield K, Pieczek A, Schainfeld R, Ramaswamy R, Kosowsky B D: Combined physiologic and anatomic assessment of percutaneous revascularization using a Doppler guidewire and ultrasound catheter. *Am J Cardiol* 1993; 71:70D–86D 24. Bauters C, Asahara T, Zheng L P, Takeshita S, Bunting S, Ferrara N, Symes J F, Isner J M: Physiologic assessment of augmented vascularity induced by VEGF in ischemic rabbit hindlimb. *Am J Physiol* 1994; 267: H1263–H1271

25. Losordo D W, Pickering J G, Takeshita S, Leclerc G, Gal D, Weir L, Kearney M, Jekanowski J, Isner J M: Use of the rabbit ear artery to serially assess foreign protein secretion after site specific arterial gene transfer in vivo: Evidence that anatomic identification of successful gene transfer may underestimate the potential magnitude of transgene expression. *Circulation* 1994; 89: 785–792

26. Riessen R, Rahimizadeh H, Blessing E, Takeshita S, Barry J J, Isner J M: Arterial gene transfer using pure DNA applied directly to a hydrogel-coated angioplasty balloon. *Hum Gene Ther* 1993; 4: 749–758

27. Isner J M, Pieczek A, Schainfeld R, Blair R, Haley L, Asahara T, Rosenfield K, Razvi S, Walsh K, Symes J: Clinical evidence of angiogenesis following arterial gene transfer of phVEGF165. *Lancet* 1996; 348: 370–374

28. Nab el E G, Plautz G, Nab el G J: Transduction of a foreign histocompatibility gene into the arterial wall induces vasculitis. *Proc Natl Acad Sci USA* 1992; 89: 5157–5161

29. Nabel E G, Yang Z, Liptay S, San H, Gordon D, Haudenschild C C, Nabel G J: Recombinant platelet denved growth factor B gene expression in porcine arteries induces intimal hyperplasia in vivo. *J Clin Invest* 1993; 91: 1822–1829

30. Nabel E G, Yang Z Y, Plautz G, Forough R, Zhan X, Haudenschild C C, Maciag T, Nabel G J: Recombinant fibroblast growth factor-1 promotes intimal hyperplasia and angiogenesis in arteries in vivo. *Nature* 1993; 362: 844–846

31. Takeshita S, Losordo D W, Kearney M, Isner J M: Time course of recombinant protein secretion following liposome-mediated gene transfer in a rabbit arterial organ culture model. *Lab Invest* 1994; 71: 387–391

32. Tsurumi Y, Takeshita S, Chen D, Kearney M, Rossow S T, Passeri J, Horowitz J R, Symes J F: Direct intramuscular gene transfer of naked DNA encoding vascular endothelial growth factor augments collateral development and tissue perfusion. *Circulation* 1996; 94: 3281–3290

33. Takeshita S, Isshiki T, Sato T: Increased expression of direct gene transfer into skeletal muscles observed after acute ischemic injury in rats. *Lab Invest* 1996; 74: 1061–1065

34. Gal D, Weir L, Leclerc G, Pickering J G, Hogan J, Isner J M: Direct myocardial transfection in two animal models: Evaluation of parameters affecting gene expression and percutaneous gene delivery. *Lab Invest* 1993; 68: 18–25

35. Oswald H, Heinemann F, Nikol S, Salmons B, Gunzburg W-H: Removal of an inhibitor of marker enzyme activity in artery extracts by chelating agents. *Biotechniques* 1997; 22: 78–81

36. Tsurumi Y, Murohara T, Krasinski K, Dongfen C, Witzenbichler B, Kearney M, Couffinhal T, Isner J M: Reciprocal Relationship Between VEGF and NO in the Regulation of Endothelial Integrity. *Nature Med* 1997; 3: 879–886

37. Rentrop K P, Cohen M, Blanke H, Phillips R A: Changes in coronary collateral filling immediately after controlled coronary artery occlusion by an angioplasty balloon in human subjects. *J Am Coll Cardiol* 1985; 5: 587–592

38. Gibson C M, Cannon C P, Daley W L, Dodge J T, Alexander B, Marble S J, McCabe C H, Raymond L, Fortin T, Poole W K, Braunwald E, for the TIMI 4 Study Group: TIMI frame count: A quantitative method of assessing coronary artery flow. *Circulation* 1996; 93: 879–888

39. Tischer E, Mitchell R, Hartmann T, Silva M, Gospodarowicz D, Fiddes J, Abraham J: The human gene for vascular endothelial growth factor: multiple protein forms are encoded through alternative exon splicing. *J Biol Chem* 1991; 266: 11947–11954

40. Nabel G: Proposed amendment to Appendix D of the NIH Guidelines Regarding a Human Gene Therapy Protocol Entitled Immunotherapy of Malignancy by In Vivo Gene Transfer into Tumors. *Human Gene Ther* 1994; 5: 236–240

41. CBO/DNF Consensus Diabetische Voet, 1997

42. The foot in diabetes. Boulton A.

43. Bouter K P, Storm A J, Groot R, Uitslager R, Erkelens D W, Diepersloot R J A, et al. The diabetic foot in Dutch hospitals: epidemiological features and clinical outcome. *Eur J Med* 1993; 2: 215–218

44. Second European Consensus Document on Chronic Critical Leg ischemia. *Circulation* 1991; 84 (suppl. 4): 5–10

45. Baker J D, Dix D: Variability of Doppler ankle pressures with arterial occlusive disease: an evaluation of ankle index and brachial-ankle pressure gradient. *Surgery* 1981; 89: 134–137

46. Carter S A: Role of pressure measurements. In: Bernstein E F. Vascular diagnosis. 4th Edition. Mosby, St Louis etc, 1993. ISBN 0-8016-6557-4

47. Andriessen MPHM: Het effect van looptraining bij patienten met claudicatio intermittens. Thesis. Krips Repro, Meppel, 1986

48. Yao J S T: Peripheral arterial disease: evaluation in pre-, intra-, and postoperative states. In: Felix W. R. Jr. Non-invasive diagnosis of peripheral vascular disease. Raven Press, New York, 1988

49. Baker J D, Dix D: Variability of Doppler ankle pressures with arterial occlusive disease: an evaluation of ankle index and brachial-ankle pressure gradient. *Surgery* 1981; 89: 134–137

50. Fowkes F G R, et al: Variability of ankle and brachial systolic pressures in the measurement of atherosclerotic peripheral arterial disease. *J Epidemiol Community Health* 1988; 42: 128–133

51. Perayaka T, Tikkanen H, Van Knorring J, Lepantalo M: Poor reproducibility of exercise test in assessment of claudication. *Clin Physiol* 1998; 18: 187–193

52. Wijngaarden J van, Smit A J, Graeff P A de, Gilst W H van, Broek S A J van der, Veldhuisen D J van, Lie K I, Wesseling H: The effects of acetylsalicylic acid on peripheral haemodynamics in patients with chronic congestive heart failure treated with ACE inhibitors. *J Cardiouasc Pharmacol* 1994; 23: 240–245

53. Broek S A J van den, Graeff P A de, Smit A J, Girbes A M J, Journée L, Gilst W H van, Hillege H L, Wesseling H, Lie K I: Effects of spirapril and captopril on regional blood flow in chronic congestive heart failure; a comparison between a short- and long-acting angiotensin-converting enzyme inhibitor. *J Cardiouasc Pharm* 1995; 25: 105–112

54. Gosselink A T M, Smit A J, Crijns H J G M, Hillege H L, Lie K I: Alteration of peripheral vasodilatory reserve capacity after cardioversion of atrial fibrillation. *Eur Heart J* 1996; 17: 926–934

55. Nilsson G E, Tenland T, Oberg P A: A new instrument for continuous measurement of tissue blood flow by light beating spectroscopy. IEEE Trans Biomed Eng 1980; 27: 597–604
56. Belcaro G, Nicolaides A N: The predictive value of laser Doppler measurements in diabetic microangiopathy and foot ulcers. In: Bernstein E F. Vascular diagnosis. 4th Edition. Mosby, St Louis etc, 1993. ISBN 0-8016-6557-4
57. Dompeling E C, Smit A J: Assessment of pinacidil in patients with primary Raynaud's phenomenon. *VASA* 1992; suppl. 34: 34–37
58. Van de Ven L L M, Van Leeuwen J T M, Smit A J: The influence of chronic treatment with betablockade and angiotensin converting enzyme inhibition on the peripheral blood flow in hypertensive patients with and without concomitant intermittent claudication. A comparative cross-over trial. *VASA* 1994; 23: 357–362
59. Bollinger A., Frey J, Jaeger K, Furrer J, Seglias J, and Siegenthaler W: Patterns of diffusion through skin capillaries in patients with long-term diabetes. *N Engl J Med* 1982; 307: 1305–1310
60. Jager J J, Oomen P H N, Sluiter W J, Reitsma W D, Smit A J: Improved reproducibility of the 'large-window' method of assessing transcapillary and interstitial fluorescein diffusion in the skin in healthy subjects and in subjects with insulin-dependent diabetes mellitus. *Int J Microcirc* 1997; 17: 150–158
61. Jager J J, Tromp A, Hooymans J M M, Reitsma W D, Smit A J: Reproducibility of vitreous fluorophotometry in patients with type I diabetes mellitus. *Ophtalmologica* 1997; 211: 209–213
62. Jager J J, Oomen P H N, Hoogenberg K, Dullaart R P F, Reitsma W D, Smit A: Abnormal fluorescein diffusion in type 1 diabetic subjects with and without microalbuminuria. *Int J Microcircul:* Clin Experim 1998
63. Klomp H M, Spincemaille G H J J, Steyerberg E W, Habbema J D F, Van Urk H: Spinal-cord stimulation in critical limb ischemia: a randomised trial. *Lancet* 1999; 353: 1040–1044.
64. Sclikryemann R O, Van Hinsbergh V W: Pole vascular permeability factor/vascular endothelial growth factor in eye disease. *Br J Ophthalmol* 1997; 81: 501–512
65. Adamis A P: Increased vascular endothelial growth factor levels in the vitreous of eyes with proliferative diabetic retinopathy. *Am J Ophthalinol* 1994; 118: 445–450
66. Tolentino M J. Vascular endothelial growth factor is sufficient to produce iris neovascularization and neovascularization glaucoma in a nonhuman primate. *Arch*

The invention claimed is:

1. A vector comprising a DNA sequence encoding human vascular endothelial growth factor, wherein said nucleic acid sequence comprises nucleotides 682–1258 of SEQ ID NO: 6 operably linked to a modified pCMV promoter of nucleotides 14–619 of SEQ ID NO: 6.

2. An isolated host cell which comprises a vector according to claim 1.

3. An isolated host cell according to claim 2, which is a human cell.

4. A composition comprising a vector according to claim 1.

5. A pharmaceutical composition comprising a vector according to claim 1 and a pharmaceutically acceptable carrier.

6. A method of treatment of arterial diseases, comprising intramuscularly administering a vector according to claim 1 with a carrier to a suitable recipient, wherein production of said VEGF results in an increase in the number of collateral blood vessels in ischemic tissues and/or improved blood flow.

7. A method of treatment of arterial diseases, comprising intramuscularly administering a composition according to claim 4 or 5 to a suitable recipient, wherein production of said VEGF results in an increase in the number of collateral blood vessels in ischemic tissues and/or improved blood flow.

* * * * *

SEQUENCE LISTING

```
<160> NUMBER OF SEQ ID NOS: 6

<210> SEQ ID NO 1
<211> LENGTH: 9
<212> TYPE: DNA
<213> ORGANISM: Artificial Sequence
<220> FEATURE:
<223> OTHER INFORMATION: Insertion in PCMV promoter
<220> FEATURE:
<221> NAME/KEY: misc_feature
<223> OTHER INFORMATION: (1)..(9)

<400> SEQUENCE: 1 acgcgcgct                                                                    9

<210> SEQ ID NO 2
<211> LENGTH: 33
<212> TYPE: DNA
<213> ORGANISM: Artificial Sequence
<220> FEATURE:
<223> OTHER INFORMATION: PCR-forward primer
<220> FEATURE:
<221> NAME/KEY: misc_feature
<223> OTHER INFORMATION: (1)..(33)

<400> SEQUENCE: 2
atcgacatcc agtcaaagcc acgttgtgtc tca                                         33

<210> SEQ ID NO 3
<211> LENGTH: 27
<212> TYPE: DNA
<213> ORGANISM: Artificial Sequence
<220> FEATURE:
<223> OTHER INFORMATION: PCR reverse primer
<220> FEATURE:
<221> NAME/KEY: misc_feature
<223> OTHER INFORMATION: (1)..(27)

<400> SEQUENCE: 3
```

| atagcatgcg agttttcgcc ccgaaga | | 27 |

<210> SEQ ID NO 4
<211> LENGTH: 31
<212> TYPE: DNA
<213> ORGANISM: Artificial Sequence
<220> FEATURE:
<223> OTHER INFORMATION: forward primer
<220> FEATURE:
<221> NAME/KEY: misc_feature
<223> OTHER INFORMATION: (1)..(31)

<400> SEQUENCE: 4

| gcggactagt gctgtccctc ttctcttatg a | | 31 |

<210> SEQ ID NO 5
<211> LENGTH: 31
<212> TYPE: DNA
<213> ORGANISM: Artificial Sequence
<220> FEATURE:
<223> OTHER INFORMATION: backward primer
<220> FEATURE:
<221> NAME/KEY: misc_feature
<223> OTHER INFORMATION: (1)..(31)

<400> SEQUENCE: 5

| gccgacgtgc agtctaggtg aagatccttt t | | 31 |

<210> SEQ ID NO 6
<211> LENGTH: 5875
<212> TYPE: DNA
<213> ORGANISM: Artificial Sequence
<220> FEATURE:
<223> OTHER INFORMATION: plasmid ph VEGF165.MB sequence
<220> FEATURE:
<221> NAME/KEY: misc_feature
<223> OTHER INFORMATION: (1)..(5875)

<400> SEQUENCE: 6

| gaattcgagc tcgccccgtt acataactta cggtaaatgg cccgcctggc tgaccgccca | 60 |
| acgaccccg cccattgacg tcaataatga cgtatgttcc catagtaacg ccaatagga | 120 |
| ctttccattg acgtcaatgg gtggagtatt tacggtaaac tgcccacttg gcagtacatc | 180 |
| aagtgtatca tatgccaagt acgcccccta ttgacgtcaa tgacggtaaa tggcccgcct | 240 |
| ggcattatgc ccagtacatg accttatggg actttcctac ttggcagtac atctacgcgc | 300 |
| gctacgtatt agtcatcgct attaccatgg tgatgcggtt ttggcagtac atcaatgggc | 360 |
| gtggatagcg gtttgactca cggggatttc caagtctcca ccccattgac gtcaatggga | 420 |
| gtttgttttg gcaccaaaat caacgggact ttccaaaatg tcgtaacaac tccgccccat | 480 |
| tgacgcaaat gggcggtagg cgtgtacggt gggaggtcta tataagcaga gctcgtttag | 540 |
| tgaaccgtca gatcgcctgg agacgccatc cacgctgttt tgacctccat agaagacacc | 600 |
| gggaccgatc cagcctccgg gggatcttgg tggcgtgaaa ctcccgcacc tcttcggcca | 660 |
| gcgccttgta gaagcgcgta cgatgaactt tctgctgtct tgggtgcatt ggagccttgc | 720 |
| cttgctgctc tacctccacc atgccaagtg gtcccaggct gcacccatgg cagaaggagg | 780 |
| agggcagaat catcacgaag tggtgaagtt catggatgtc tatcagcgca gctactgcca | 840 |
| tccaatcgag accctggtgg acatcttcca ggagtaccct gatgagatcg agtacatctt | 900 |
| caagccatcc tgtgtgcccc tgatgcgatg cggggctgc tgcaatgacg agggcctgga | 960 |
| gtgtgtgccc actgaggagt ccaacatcac catgcagatt atgcggatca aacctcacca | 1020 |

```
aggccagcac ataggagaga tgagcttcct acagcacaac aaatgtgaat gcagaccaaa    1080
gaaagataga gcaagacaag aaaatccctg tgggccttgc tcagagcgga gaaagcattt    1140
gtttgtacaa gatccgcaga cgtgtaaatg ttcctgcaaa aacacagact cgcgttgcaa    1200
ggcgaggcag cttgagttaa acgaacgtac ttgcagatgt gacaagccga ggcggtgagg    1260
atcctgagaa cttcagggtg agtttgggga cccttgattg ttctttcttt ttcgctattg    1320
taaaattcat gttatatgga gggggcaaag ttttcagggt gttgtttaga atgggaagat    1380
gtcccttgta tcaccatgga ccctcatgat aattttgttt ctttcacttt ctactctgtt    1440
gacaaccatt gtctcctctt attttctttt cattttctgt aacttttctcg ttaaacttta    1500 gcttgcattt gtaacgaatt tttaaattca cttttgttta tttgtcagat tgtaagtact    1560
ttctctaatc acttttttt caaggcaatc agggtatatt atattgtact tcagcacagt    1620
tttagagaac aattgttata attaaatgat aaggtagaat atttctgcat ataaattctg    1680
gctggcgtgg aaatattctt attggtagaa acaactacac cctggtcatc atcctgcctt    1740
tctctttatg gttacaatga tatacactgt ttgagatgag gataaaatac tctgagtcca    1800
aaccgggccc ctctgctaac catgttcatg ccttcttctc tttcctacag ctcctgggca    1860
acgtgctggt tgttgtgctg tctcatcatt ttggcaaaga attcactcct caggtgcagg    1920
ctgcctatca gaaggtggtg gctggtgtgg ccaatgccct ggctcacaaa taccactgag    1980 atcttttcc ctctgccaaa aattatgggg acatcatgaa gccccttgag catctgactt    2040
ctggctaata aaggaaattt attttcattg caatagtgtg ttggaatttt ttgtgtctct    2100
cactcggaag gacatatggg agggcaaatc atttaaaaca tcagaatgag tatttggttt    2160
agagtttggc aacatatgcc catatgctgg ctgccatgaa caaaggttgg ctataaagag    2220
gtcatcagta tatgaaacag cccctgctg tccattcctt attccataga aaagccttga    2280
cttgaggtta gatttttttt atattttgtt ttgtgttatt ttttctttta acatccctaa    2340
aattttcctt acatgtttta ctagccagat ttttcctcct ctcctgacta ctcccagtca    2400
tagctgtccc tcttctctta tggagatccc tcgaggagct ttttgcaaaa gcctaggtaa    2460
tgaatcggcc aacgcgcggg gagaggcggt ttgcgtattg ggcgctcttc cgcttcctcg    2520
ctcactgact cgctgcgctc ggtcgttcgg ctgcggcgag cggtatcagc tcactcaaag    2580
gcggtaatac ggttatccac agaatcaggg gataacgcag gaaagaacat gtgagcaaaa    2640
ggccagcaaa aggccaggaa ccgtaaaaag gccgcgttgc tggcgttttt ccataggctc    2700
cgcccccctg acgagcatca caaaaatcga cgctcaagtc agaggtggcg aaacccgaca    2760
ggactataaa gataccaggc gtttccccct ggaagctccc tcgtgcgctc tcctgttccg    2820
accctgccgc ttaccggata cctgtccgcc tttctccctt cgggaagcgt ggcgctttct    2880
catagctcac gctgtaggta tctcagttcg gtgtaggtcg ttcgctccaa gctgggctgt    2940
gtgcacgaac cccccgttca gcccgaccgc tgcgccttat ccggtaacta tcgtcttgag    3000
tccaacccgg taagacacga cttatcgcca ctggcagcag ccactggtaa caggattagc    3060
agagcgaggt atgtaggcgg tgctacagag ttcttgaagt ggtggcctaa ctacggctac    3120
actagaagaa cagtatttgg tatctgcgct ctgctgaagc cagttacctt cggaaaaaga    3180
gttggtagct cttgatccgg caaacaaacc accgctggta gcggtggttt ttttgtttgc    3240
aagcagcaga ttacgcgcag aaaaaaagga tctcaagaag atcctttgat cttttctacg    3300
gggtctgacg ctcagtggaa cgaaaactca cgttaaggga ttttggtcat gagattatca    3360
aaaaggatct tcacctagac tgccagtcaa agccacgttg tgtctcaaaa tctctgatgt    3420
```

```
tacattgcac aagataaaaa tatatcatca tgaacaataa aactgtctgc ttacataaac    3480
agtaatacaa ggggtgttat gagccatatt caacgggaaa cgtcttgctc gaggccgcga    3540
ttaaattcca acatggatgc tgatttatat gggtataaat gggctcgcga taatgtcggg    3600
caatcaggtg cgacaatcta tcgattgtat gggaagcccg atgcgccaga gttgtttctg    3660
aaacatggca aagtagcgt tgccaatgat gttacagatg atgggtcag actaaactgg      3720
ctgacggaat ttatgcctct tccgaccatc aagcatttta tccgtactcc tgatgatgca    3780
tggttactca ccactgcgat ccccgggaaa acagcattcc aggtattaga agaatatcct   3840
gattcaggtg aaaatattgt tgatgcgctg gcagtgttcc tgcgccggtt gcattcgatt    3900
cctgtttgta attgtccttt taacagcgat cgcgtatttc gtctcgctca ggcgcaatca    3960
cgaatgaata acggtttggt tgatgcgagt gattttgatg acgagcgtaa tggctggcct   4020
gttgaacaag tctggaaaga atgcataag cttttgccat tctcaccgga ttcagtcgtc      4080
actcatggtg atttctcact tgataacctt attttttgacg aggggaaatt aataggttgt   4140
attgatgttg gacgagtcgg aatcgcagac cgataccagg atcttgccat cctatggaac    4200
tgcctcggtg agttttctcc ttcattacag aaacggcttt ttcaaaaata tggtattgat    4260
aatcctgata tgaataaatt gcagtttcat ttgatgctcg atgagttttt ctaatcagaa    4320
ttggttaatt ggttgtaaca ctggcagagc attacgctga cttgacggga cggcggcttt    4380
gttgaataaa tcgaactttt gctgagttga aggatcagat cacgcatctt cccgacaacg    4440
cagaccgttc cgtggcaaag caaaagttca aaatcaccaa ctggtccacc tacaacaaag    4500
ctctcatcaa ccgtggctcc ctcactttct ggctggatga tggggcgatt caggcctggt   4560
atgagtcagc aacaccttct tcacgaggca gacctcagcg ccccccccc ccgttcttcg     4620
gggcgaaaac tctcaaggat cttaccgctg ttgagatcca gttcgatgta acccactcgt   4680
gcacccaact gatcttcagc atcttttact ttcaccagcg tttctgggtg agcaaaaaca   4740
ggaaggcaaa atgccgcaaa aaagggaata agggcgacac ggaaatgttg aatactcata   4800
ctcttccttt ttcaatatta ttgaagcatt tatcagggtt attgtctcat gagcggatac   4860
atatttgaat gtatttagaa aaataaacaa ataggggttc cgcgcacatt tccccgaaaa    4920
gtgccacctg acgtctaaga aaccattatt atcatgacat taacctataa aaataggcgt   4980
atcacgaggc cctttcgtct cgcgcgtttc ggtgatgacg gtgaaaacct ctgacacatg    5040
cagctcccgg agacggtcac agcttgtctg taagcggatg ccgggagcag acaagcccgt    5100
cagggcgcgt cagcgggtgt tggcgggtgt cggggctggc ttaactatgc ggcatcagag    5160
cagattgtac tgagagtgca ccatatgcgg tgtgaaatac cgcacagatg cgtaaggaga    5220
aaataccgca tcaggaaatt gtaagcgtta atattttgtt aaaattcgcg ttaaattttt   5280
gttaaatcag ctcattttttt aaccaatagg ccgaaatcgg caaaatccct tataaatcaa   5340
aagaatagac cgagataggg ttgagtgttg ttccagtttg gaacaagagt ccactattaa    5400
agaacgtgga ctccaacgtc aaaggggcgaa aaaccgtcta tcagggcgat ggcccactac    5460
gtgaaccatc accctaatca agttttttgg ggtcgaggtg ccgtaaagca ctaaatcgga    5520
accctaaagg gagccccga tttagagctt gacggggaaa gccggcgaac gtggcgagaa     5580
aggaagggaa gaaagcgaaa ggagcgggcg ctagggcgct ggcaagtgta gcggtcacgc    5640
tgcgcgtaac caccacccc gccgcgctta atgcgccgct acaggcgcg tccattcgcc      5700
attcaggctg cgcaactgtt gggaagggcg atcggtgcgg gcctcttcgc tattacgcca    5760
```

```
gctggcgaaa gggggatgtg ctgcaaggcg attaagttgg gtaacgccag ggtttccca      5820 gtcacgacgt tgtaaaacga cggccagtga attgtaatac gactcactat agggc          5875
```